(12) United States Patent
DiNinno et al.

(10) Patent No.: US 7,138,426 B2
(45) Date of Patent: *Nov. 21, 2006

(54) ESTROGEN RECEPTOR MODULATORS

(75) Inventors: Frank P. DiNinno, Old Bridge, NJ (US); Timothy Allen Blizzard, Middletown, NJ (US); Jerry Dwain Morgan, II, Sayreville, NJ (US)

(73) Assignee: Merck & Co., Inc., Rahway, NJ (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/512,172

(22) PCT Filed: Apr. 18, 2003

(86) PCT No.: PCT/US03/12103

§ 371 (c)(1),
(2), (4) Date: Oct. 21, 2004

(87) PCT Pub. No.: WO03/091239

PCT Pub. Date: Nov. 6, 2003

(65) Prior Publication Data

US 2005/0234245 A1    Oct. 20, 2005

(51) Int. Cl.
*A61K 31/4025*    (2006.01)
*C07D 411/12*    (2006.01)

(52) U.S. Cl. .................... 514/422; 548/526; 548/527; 514/434

(58) Field of Classification Search ................ 548/526, 548/527
See application file for complete search history.

(56) References Cited

U.S. PATENT DOCUMENTS 5,919,814 A    7/1999    Guillaumet et al.
6,013,607 A    1/2000    Otten et al.

FOREIGN PATENT DOCUMENTS

WO    WO 02/32373    4/2002
WO    WO 02/32377    4/2002

OTHER PUBLICATIONS

Powles, T.J. "Breast Cancer Prevention", The Oncologist, vol. 7 (2002), pp. 60-64.
Park, W.C. and Jordan, V.C., "Selective estrogen receptor modulators (SERMS) and their roles in breast cancer prevention", Trends in Moleecular Medicine, vol. 8, No. 2 (Feb. 2002), pp. 82-88.
Wolff, A.C. "Use of SERMs for the Adjuvant Therapy of Early-Stage Breast Cancer", Annals NY Academy of Sciences, vol. 949 (Dec. 2001), pp. 80-88.
Steiner, M.S., et al., "Selective Estrogen Receptor Modulators for the Chemoprevention of Prostate Cancer", Urology, vol. 57 (Supplement 4A) (Apr. 2001), pp. 68-72.
Campisi, C., et al., "Complete resolution of breast cancer bone metastasis through the use of beta-Interferon and Tamoxifen," Eur J Gynaecol Oncology, vol. 14, No. 6 (1993), pp. 479-483.
Ribeiro, G. and Swindell, R., "Adjuvant Tamoxifen for male breast cancer (MBC)", Br. J. Cancer (1992), vol. 65, pp. 252-254.
Jordan, V.C., et al., "Selective Estrogen Receptor Modulation and Reduction in Risk of Breast Cancer, Osteoporosis, and Coronary Heart Disease", Nat'l Cancer Inst., vol. 93, No. 19 (Oct. 2001), pp. 1449-1457.
Bjarnason, N.H., et al., "Six and twelve month changes in bone turnover are related to reduction in vertebral fracture risk during 3 years of raloxifene treatment in postmenopausal osteoporosis", Osteoporosis Int. (2001), vol. 12, pp. 922-930.
Fentiman, I.S., et al., Tamoxifen Protects Against Steroid-induced Bone Loss:, Eur. J Cancer, vol. 28, No. 2/3(1992), pp. 684-685.
Rodan, G. A., et al., "Therapeutic Approaches to Bone Diseases", Science (Sep. 2000), vol. 289, pp. 1508-1514.
Palomba, S., et al., "Effects of raloxifene treatment on uterine leiomyomas in postmenopausal women", Fertility and Sterility, vol. 76, No. 1 (Jul. 2001), pp. 38-43.
Picard, F., et al., "Effects of the estrogen antagonist EM-652.HCl on energy balance and lipid metabolism in ovariectomized rats", Int. Journal of Obesity (2000), vol. 24, pp. 830-840.
Badger, A.M., et al., "Idoxifene, a Novel Selective Estrogen Receptor Modulator, is Effective in a Rat Model of Adjuvant-Induced Arthritis", Journ. of Pharmacol and Experimental Ther. (Dec. 1999), vol. 291, No. 3, pp. 1380-1386.

(Continued)

*Primary Examiner*—Kamal A. Saeed
*Assistant Examiner*—Jason M. Nolan
(74) *Attorney, Agent, or Firm*—Nicole M. Beeler; Mark R. Daniel

(57)    ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, and cancer, in particular of the breast, uterus and prostate.

32 Claims, No Drawings

OTHER PUBLICATIONS

Goldstein, S.R., "The Effect of SERMs on the Endometrium", Annals NY Academy of Sciences, vol. 949 (2001), pp. 237-242.

Goldstein, S.R., "Raloxifene Effect on Frequency of Surgery for Pelvic Floor Relaxation", The American College of Obstet. and Gynecol., vol. 98, No. 1 (Jul. 2001), pp. 91-96.

Nuttal, M.E., et al., "Idoxifen: A Novel Selective Estrogen Receptor Modulator Prevents Bone Loss and Lowers Cholesterol Levels in Ovariectomized Rats and Decreases Uterine Weight in Intact Rats", Endocrinology (Dec. 1998), vol. 139, No. 12, pp. 5224-5234.

Guzzo, J.A., "Selective Estrogen Receptor Modulators—a New Age of Estrogens in Cardiovascular Disease?", Clin. Cardiol (2000), vol. 23, No. 1, pp. 15-17.

Simoncini, T. and Genazzani, A.R., "Direct vascular effects of estrogen and selective estrogen receptor modulators", Curr. Opinion in Obstetrics and Gynecology (Jun. 2000), vol. 12, No. 3, pp. 181-187.

Yaffe, K., et al., "Cognitive Function in Postmenopausal Women Treated with Raloxifene", N. Engl. Journal of Medicine, vol. 344, No. 16 (Apr. 2001), pp. 1207-1213.

Miller, et al., "Targeting the Estrogen Receptor ith SERMs", Annual Reports in Medicinal Chemistry (2001), vol. 36, pp. 149-158.

Paige, et al., "Estrogen Receptor (ER) Modulators Each Induce Distince Conformational Changes in ED alpha and ER beta", Proceedings of the National Academy of Sciences (Mar. 1999), vol. 96, No. 7, pp. 3999-4004.

Bendinskas, et al., "Sequence-Specific Photomodification of DNA by an Oligonucleotide-Phenanthrodihydrodioxin Conjugate", Bioconjugate Chemistry (Sep. 1998), vol. 9, No. 5, pp. 555-563.

ESTROGEN RECEPTOR MODULATORS

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

For example, estrogen-like compounds would be beneficial in the treatment and prevention of bone loss. Bone loss occurs in a wide range of subjects, including women that are post-menopausal or have had a hysterectomy, patients who were or are currently being treated with corticosteroids, and patients having gonadal dysgenesis. The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the U.S., there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Osteoporosis affects approximately 20 to 25 million postmenopausal women in the U.S. alone. It has been theorized that the rapid loss of bone mass in these women is due to the cessation of estrogen production of the ovaries. Since studies have shown that estrogen slows the reduction of bone mass due to osteoporosis, estrogen replacement therapy is a recognized treatment for post-menopausal osteoporosis.

In addition to bone mass, estrogen appears to have an effect on the biosynthesis of cholesterol and cardiovascular health. Statistically, the rate of occurrence of cardiovascular disease is roughly equal in postmenopausal women and men; however, premenopausal women have a much lower incidence of cardiovascular disease than men. Because postmenopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol.

Postmenopausal women given estrogen replacement therapy experience a return of lipid levels to concentrations comparable to levels associated with the premenopausal state. Thus, estrogen replacement therapy could be an effective treatment for such disease. However, the side effects associated with long term estrogen use limit the use of this alternative.

Other disease states that affect postmenopausal women include estrogen-dependent breast cancer and uterine cancer. Anti-estrogen compounds, such as tamoxifen, have commonly been used as chemotherapy to treat breast cancer patients. Tamoxifen, a dual antagonist and agonist of estrogen receptors, is beneficial in treating estrogen-dependent breast cancer. However, treatment with tamoxifen is less than ideal because tamoxifen's agonist behavior enhances its unwanted estrogenic side effects. For example, tamoxifen and other compounds that agonize estrogen receptors tend to increase cancer cell production in the uterus. A better therapy for such cancers would be an anti-estrogen compound that has negligible or nonexistent agonist properties.

Although estrogen can be beneficial for treating pathologies such as bone loss, increased lipid levels, and cancer, long-term estrogen therapy has been implicated in a variety of disorders, including an increase in the risk of uterine and endometrial cancers. These and other side effects of estrogen replacement therapy are not acceptable to many women, thus limiting its use.

Alternative regimens, such as a combined progestogen and estrogen dose, have been suggested in an attempt to lessen the risk of cancer. However, such regimens cause the patient to experience withdrawal bleeding, which is unacceptable to many older women. Furthermore, combining estrogen with progestogen reduces the beneficial cholesterol-lowering effect of estrogen therapy. In addition, the long term effects of progestogen treatment are unknown.

In addition to post-menopausal women, men suffering from prostatic cancer can also benefit from anti-estrogen compounds. Prostatic cancer is often endocrine-sensitive; androgen stimulation fosters tumor growth, while androgen suppression retards tumor growth. The administration of estrogen is helpful in the treatment and control of prostatic cancer because estrogen administration lowers the level of gonadotropin and, consequently, androgen levels.

The estrogen receptor has been found to have two forms: ERα and ERβ. Ligands bind differently to these two forms, and each form has a different tissue specificity to binding ligands. Thus, it is possible to have compounds that are selective for ERα or ERβ, and therefore confer a degree of tissue specificity to a particular ligand.

What is needed in the art are compounds that can produce the same positive responses as estrogen replacement therapy without the negative side effects. Also needed are estrogen-like compounds that exert selective effects on different tissues of the body. Specifically, what is needed are compounds that exhibit a potent, selective affinity for ERα, and act as antagonists on breast and uterine tissues and as agonists on bone and lipids.

The compounds of the instant invention are ligands for estrogen receptors and as such may be useful for treatment or prevention of a variety of conditions related to estrogen functioning including: bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence.

SUMMARY OF THE INVENTION

The present invention relates to compounds that are capable of treating and/or preventing a variety of conditions related to estrogen functioning. One embodiment of the present invention is illustrated by a compound of Formula I, and the pharmaceutically acceptable salts, stereoisomers, and chiral forms thereof:

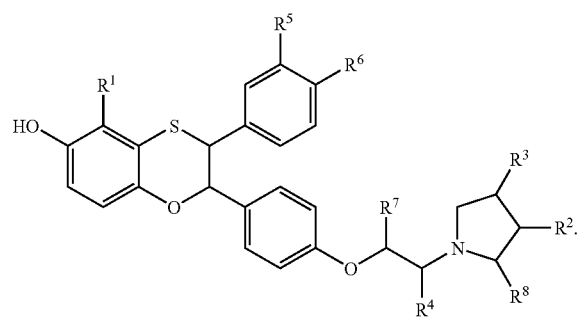

I

DETAILED DESCRIPTION OF THE INVENTION

The present invention relates to compounds useful as estrogen receptor modulators. Compounds of the present invention are described by the following chemical formula:

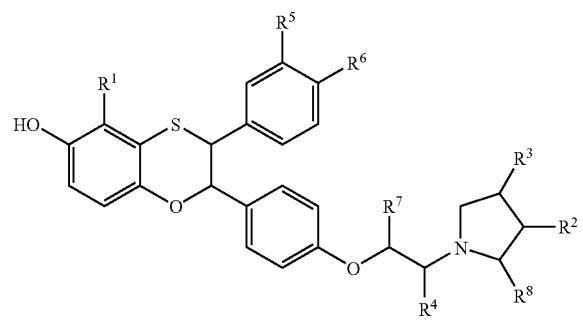

wherein $R^1$ is selected from the group consisting of hydrogen or halo;
$R^2$ is selected from hydrogen, $C_{1-3}$ alkyl, $CH_2F$, $CHF_2$ or $CF_3$;
$R^3$ is selected from hydrogen, $C_{1-3}$ alkyl, $CH_2F$, $CHF_2$ or $CF_3$;
$R^4$ is selected from $C_{1-3}$ alkyl, $CH_2F$, $CHF_2$, $CF_3$ or hydrogen with the proviso that R4 and R7 are not simultaneously hydrogen;
$R^5$ is selected from hydrogen or hydroxyl;
$R^6$ is selected from hydrogen or hydroxyl;
$R^7$ is selected from $C_{1-3}$ alkyl, $CH_2F$ or hydrogen with the proviso that $R^4$ and R7 are not simultaneously hydrogen;
$R^8$ is selected from hydrogen, $C_{1-3}$ alkyl or $CH_2F$;

or a pharmaceutically acceptable salt, stereoisomer, or chiral form thereof.

In one class of compounds of the present invention, $R^4$ is $CH_3$, or a pharmaceutically acceptable salt, stereoisomer, or chiral form thereof.

A class of compounds of the present invention is described by the chemical formula:

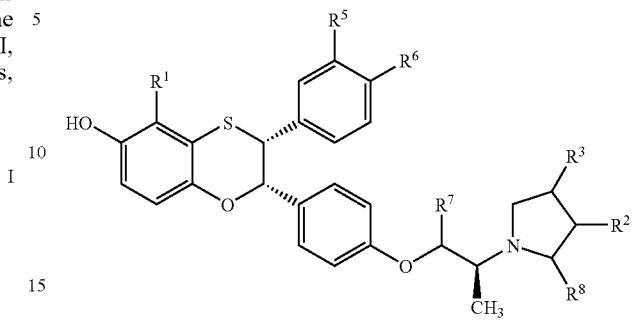

wherein $R^1$ is selected from hydrogen or halo;
$R^2$ is selected from hydrogen, $C_{1-3}$ alkyl, $CH_2F$, $CHF_2$ or $CF_3$;
$R^3$ is selected from hydrogen, $C_{1-3}$ alkyl, $CH_2F$, $CHF_2$ or $CF_3$;
$R^5$ is selected from hydrogen or hydroxyl;
$R^6$ is selected from hydrogen or hydroxyl;
$R^7$ is selected from hydrogen, $C_{1-3}$ alkyl or $CH_2F$;
$R^8$ is selected from hydrogen, $C_{1-3}$ alkyl or $CH_2F$;

or a pharmaceutically acceptable salt, stereoisomer, or chiral form thereof.

In one class of compounds of the present invention, $R^1$ is selected from the group consisting of hydrogen and fluoro.

Non-limiting examples of the present invention include:

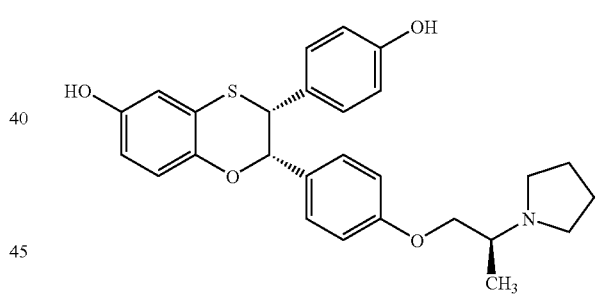

(2S,3R)-3-(4-hydroxyphenyl)-2-(4-{[(2S)-2-pyrrolidin-1-ylpropyl]oxy}phenyl)-2,3-dihydro-1,4-benzoxathiin-6-ol;

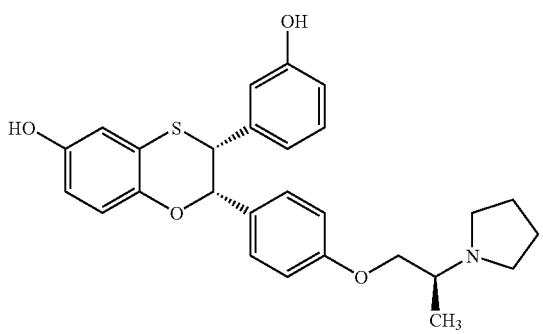

(2S,3R)-3-(3-hydroxyphenyl)-2-(4-{[(2S)-2-pyrrolidin-1-ylpropyl]oxy}phenyl)-2,3-dihydro-1,4-benzoxathiin-6-ol;

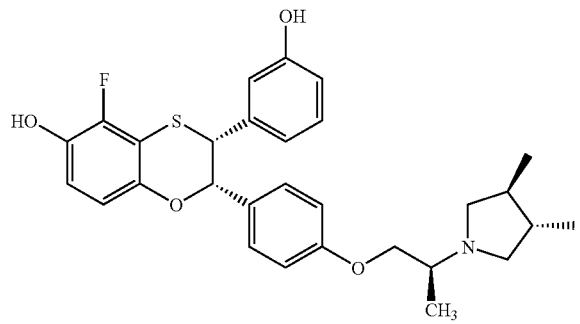

(2S,3R)-2-[4-({(2S)-2-[(3S,4S)-3,4-dimethylpyrrolidin-1-yl]propyl}oxy)phenyl]-5-fluoro-3-(3-hydroxyphenyl)-2,3-dihydro-1,4-benzoxathiin-6-ol;

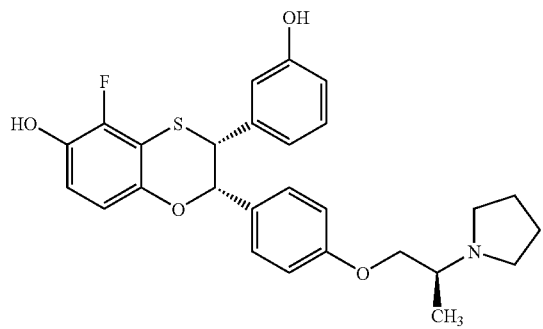

(2S,3R)-5-fluoro-3-(3-hydroxyphenyl)-2-(4-{[(2S)-2-pyrrolidin-1-ylpropyl]oxy}phenyl)-2,3-dihydro-1,4-benzoxathiin-6-ol;

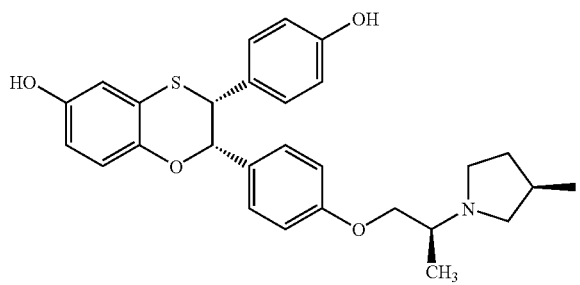

(2S,3R)-3-(4-hydroxyphenyl)-2-[4-({(2S)-2-[(3R)-3-methylpyrrolidin-1-yl]propyl}oxy)phenyl]-2,3-dihydro-1,4-benzoxathiin-6-ol;

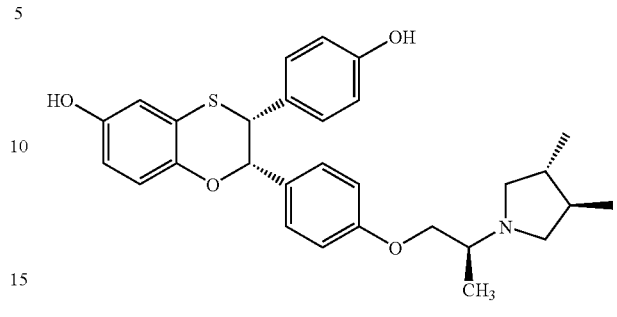

(2S,3R)-2-[4-({(2S)-2-[(3R,4R)-3,4-dimethylpyrrolidin-1-yl]propyl}oxy)phenyl]-3-(4-hydroxyphenyl)-2,3-dihydro-1,4-benzoxathiin-6-ol;

(2S,3R)-2-[4-({(2S)-2-[(3S,4S)-3,4-dimethylpyrrolidin-1-yl]propyl}oxy)phenyl]-3-(4-hydroxyphenyl)-2,3-dihydro-1,4-benzoxathiin-6-ol;

(2S,3R)-2-[4-({(2S)-2-[(3R,4S)-3,4-dimethylpyrrolidin-1-yl]propyl}oxy)phenyl]-3-(4-hydroxyphenyl)-2,3-dihydro-1,4-benzoxathiin-6-ol;

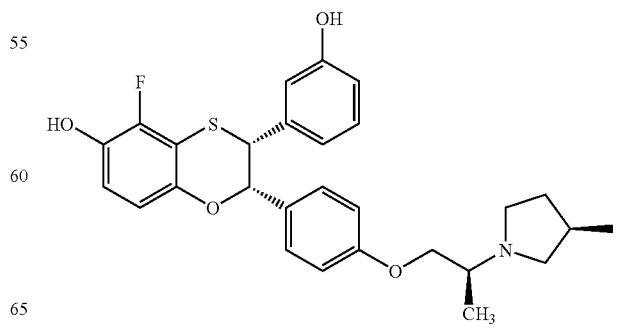

(2S,3R)-5-fluoro-3-(3-hydroxyphenyl)-2-[4-({(2S)-2-[(3R)-3-methylpyrrolidin-1-yl]propyl}oxy)phenyl]-2,3-dihydro-1,4-benzoxathiin-6-ol;

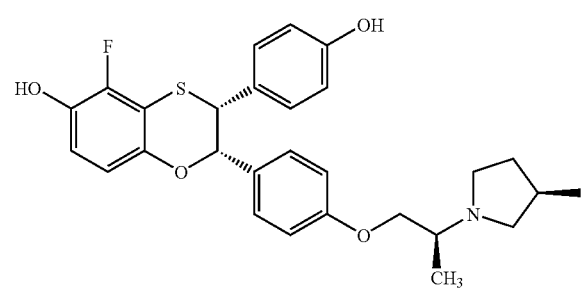

(2S,3R)-5-fluoro-3-(4-hydroxyphenyl)-2-[4-({(2S)-2-[(3R)-3-methylpyrrolidin-1-yl]propyl}oxy)phenyl]-2,3-dihydro-1,4-benzoxathlin-6-ol;

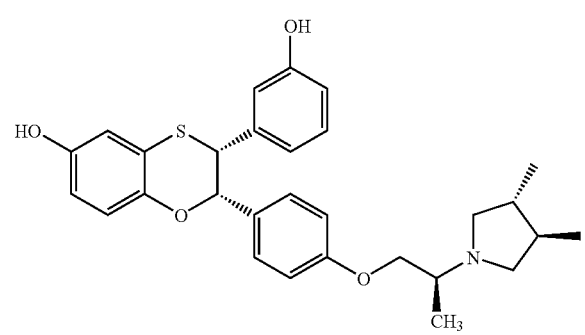

(2S,3R)-2-[4-({(2S)-2-[(3R,4R)-3,4-dimethylpyrrolidin-1-yl]propyl}oxy)phenyl]-3-(3-hydroxyphenyl)-2,3-dihydro-1,4-benzoxathiin-6-ol;

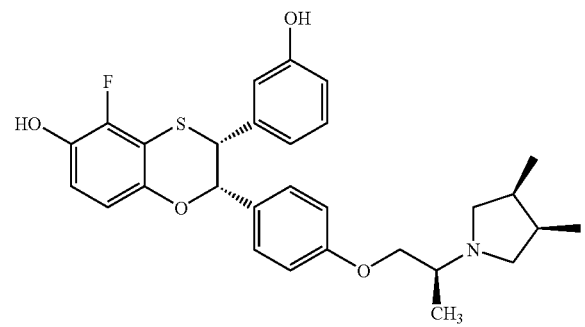

(2S,3R)-2-[4-({(2S)-2-[(3R,4S)-3,4-dimethylpyrrolidin-1-yl]propyl}oxy)phenyl]-5-fluoro-3-(3-hydroxyphenyl)-2,3-dihydro-1,4-benzoxathiin-6-ol;

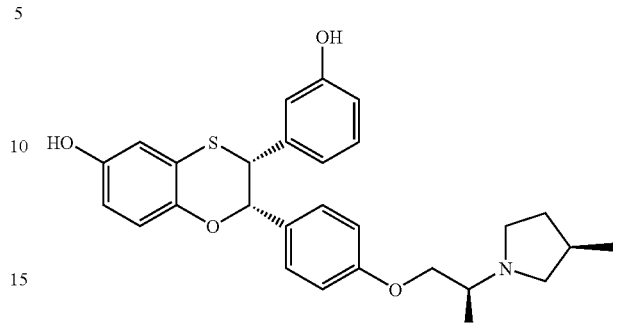

(2S,3R)-3-(3-hydroxyphenyl)-2-[4-({(2S)-2-[(3R)-3-methylpyrrolidin-1-yl]propyl}oxy)phenyl]-2,3-dihydro-1,4-benzoxathiin-6-ol;

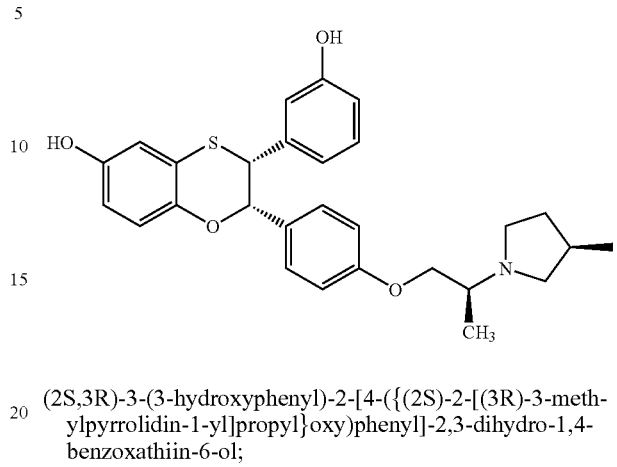

(2S,3R)-3-(4-hydroxyphenyl)-2-[4-({(2S)-2-[(3S)-3-methylpyrrolidin-1-yl]propyl}oxy)phenyl]-2,3-dihydro-1,4-benzoxathiin-6-ol;

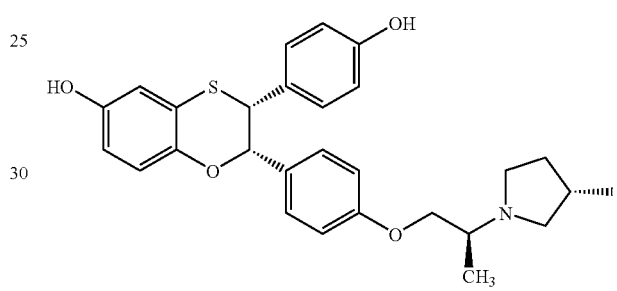

(2S,3R)-3-(3-hydroxyphenyl)-2-[4-({(2S)-2-[(3S)-3-methylpyrrolidin-1-yl]propyl}oxy)phenyl]-2,3-dihydro-1,4-benzoxathiin-6-ol;

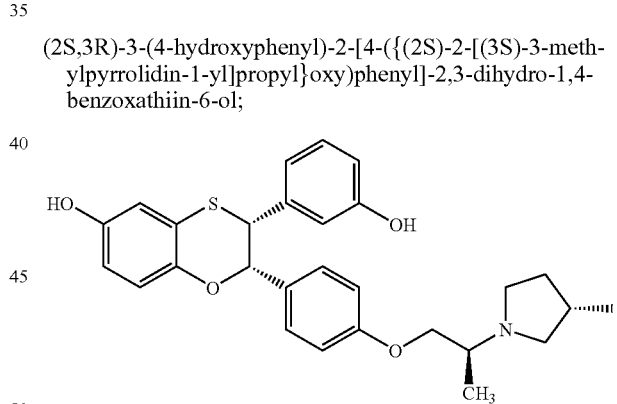
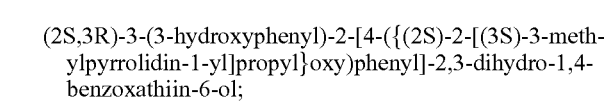
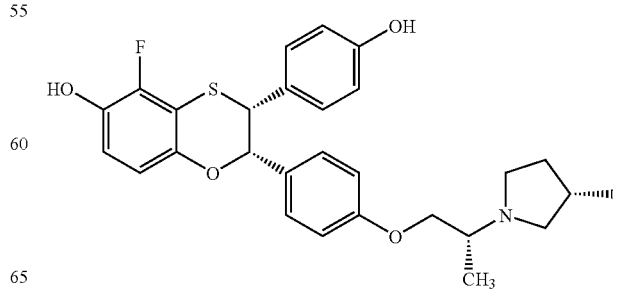

(2S,3R)-5-fluoro-3-(4-hydroxyphenyl)-2-[4-({(2R)-2-[(3S)-3-methylpyrrolidin-1-yl]propyl-}oxy)phenyl]-2,3-dihydro-1,4-benzoxathiin-6-ol;

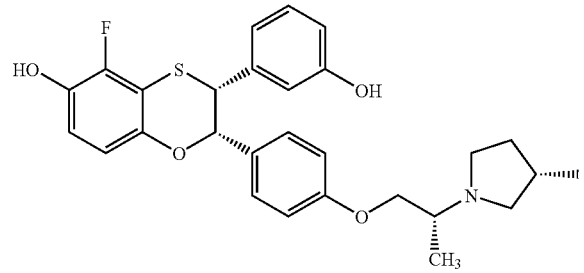

(2S,3R)-5-fluoro-3-(3-hydroxyphenyl)-2-[4-({(2R)-2-[(3S)-3-methylpyrrolidin-1-yl]propyl}oxy)phenyl]-2,3-dihydro-1,4-benzoxathiin-6-ol;

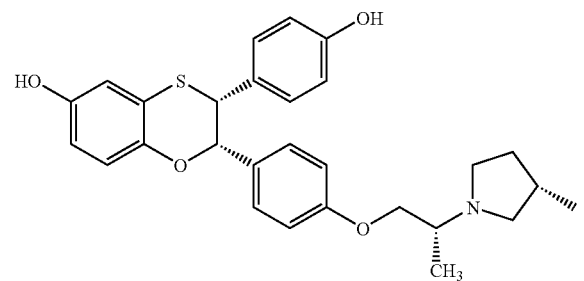

(2S,3R)-3-(4-hydroxyphenyl)-2-[4-({(2R)-2-[(3S)-3-methylpyrrolidin-1-yl]propyl}oxy)phenyl]-2,3-dihydro-1,4-benzoxathiin-6-ol;

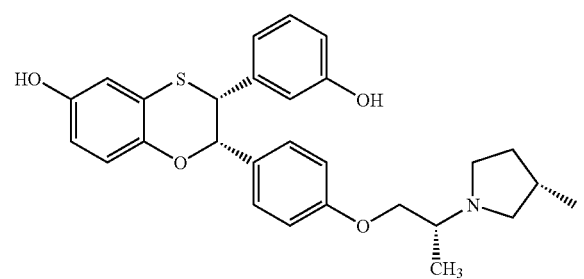

(2S,3R)-3-(3-hydroxyphenyl)-2-[4({(2R)-2-[(3S)-3-methylpyrrolidin-1-yl]propyl}oxy)phenyl]-2,3-dihydro-1,4-benzoxathiin-6-ol;

and the pharmaceutically acceptable salts, stereoisomers and chiral forms thereof.

A class of compounds of the present invention is described by the chemical formula:

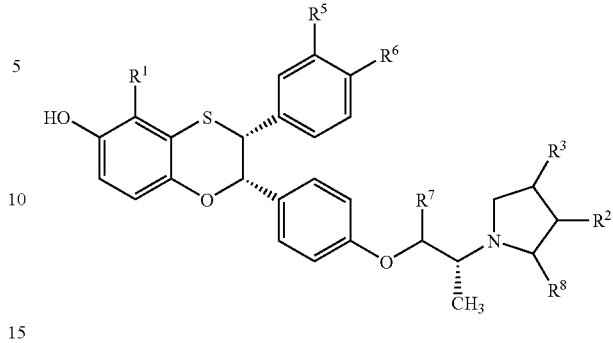

wherein $R^1$ is selected from hydrogen or halo;

$R^2$ is selected from hydrogen, $C_{1-3}$ alkyl, $CH_2F$, $CHF_2$ or $CF_3$;

$R^3$ is selected from hydrogen, $C_{1-3}$ alkyl, $CH_2F$, $CHF_2$ or $CF_3$;

$R^5$ is selected from hydrogen or hydroxyl;

$R^6$ is selected from hydrogen or hydroxyl;

$R^7$ is selected from hydrogen, $C_{1-3}$ alkyl or $CH_2F$;

$R^8$ is selected from hydrogen, $C_{1-3}$ alkyl or $CH_2F$;

or a pharmaceutically acceptable salt, stereoisomer, or chiral form thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. The present invention also relates to methods for making the pharmaceutical compositions of the present invention. The present invention is also related to processes and intermediates useful for making the compounds and pharmaceutical compositions of the present invention. These and other aspects of the invention will be apparent from the teachings contained herein.

Utilities

The compounds of the present invention are selective modulators of estrogen receptors and are therefore useful to treat or prevent a variety of diseases and conditions related to estrogen receptor functioning in mammals, preferably humans. Specifically, the compounds of the present invention exhibit a potent, selective affinity for ERα. They also act as antagonists on breast and uterine tissue and as agonists on bone and lipids. The compounds of the present invention impart a substantially greater antagonism of estradiol, while exhibiting substantially less agonism on uterine tissue, without loss of receptor affinity or selectivity, as compared to previously known compounds.

"A variety of diseases and conditions related to estrogen receptor functioning" includes, but is not limited to, bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention. The estrogen receptor antagonizing effect can be either an ERα antagonizing effect, an ERβ antagonizing effect or a mixed ERα and ERβ antagonizing effect.

The present invention also relates to methods for eliciting an estrogen receptor agonizing effect in a mammal in need thereof by administering the compounds and pharmaceutical compositions of the present invention. The estrogen receptor agonizing effect can be either an ERα agonizing effect, an ERβ agonizing effect or a mixed ERα and ERβ agonizing effect.

The present invention also relates to methods for treating or preventing disorders related to estrogen functioning, bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence in a mammal in need thereof by administering the compounds and pharmaceutical compositions of the present invention. Exemplifying the invention is a method of treating or preventing osteoporosis. Exemplifying the invention is a method of treating or preventing bone loss. Exemplifying the invention is a method of treating or preventing metastatic bone disease. Exemplifying the invention is a method of treating or preventing cancer. Exemplifying the invention is a method of treating or preventing cardiovascular disease.

An embodiment of the invention is a method for treating or preventing cancer, especially of the breast, uterus or prostate, in a mammal in need thereof by administering the compounds and pharmaceutical compositions of the present invention. The utility of SERMs for the treatment of breast, uterine or prostate cancer is known in the literature, see T. J. Powles, "Breast cancer prevention," Oncologist 2002; 7(1): 60–4; Park, W. C. and Jordan, V. C., "Selective estrogen receptor modulators (SERMS) and their roles in breast cancer prevention." Trends Mol Med. 2002 February;8(2): 82–8; Wolff, A. C. et al., "Use of SERMs for the adjuvant therapy of early-stage breast cancer," Ann N Y Acad Sci. 2001 December;949:80–8; Steiner, M. S. et al., "Selective estrogen receptor modulators for the chemoprevention of prostate cancer," Urology 2001 April; 57(4 Suppl 1):68–72.

Another embodiment of the invention is a method of treating or preventing metastatic bone disease in a mammal in need thereof by administering to the mammal a therapeutically effective amount of any of the compounds or pharmaceutical compositions described above. The utility of SERMs in the treatment of metastatic bone disease is known in the literature, see, Campisi, C. et al., "Complete resoultion of breast cancer bone metastasis through the use of beta-interferon and tamoxifen," Eur J Gynaecol Oncol 1993;14 (6):479–83.

Another embodiment of the invention is a method of treating or preventing gynecomastia in a mammal in need thereof by administering to the mammal a therapeutically effective amount of any of the compounds or pharmaceutical compositions described above. The utility of SERMs in the treatment of gynecomastia is known in the literature, see, Ribeiro, G. and Swindell R., "Adjuvant tamoxifen for male breast cancer." Br J Cancer 1992; 65:252–254; Donegan, W., "Cancer of the Male Breast," JGSM Vol. 3, Issue 4, 2000.

Another embodiment of the invention is a method of treating or preventing post-menopausal osteoporosis, glucocorticoid osteoporosis, hypercalcemia of malignancy, bone loss and bone fractures in a mammal in need thereof by administering to the mammal a therapeutically effective amount of any of the compounds or pharmaceutical compositions described above. The utility of SERMs to treat or prevent osteoporosis, hypercalcemia of malignancy, bone loss or bone fractures is known in the literature, see Jordan, V. C. et al., "Selective estrogen receptor modulation and reduction in risk of breast cancer, osteoporosis and coronary heart disease," Natl Cancer Inst 2001 October; 93(19): 1449–57; Bjarnason, N H et al., "Six and twelve month changes in bone turnover are realted to reduction in vertebral fracture risk during 3 years of raloxifene treatment in postemenopausal osteoporosis," Osteoporosis Int 2001; 12(11):922–3; Fentiman I. S., "Tamoxifen protects against steroid-induced bone loss," Eur J Cancer 28:684–685 (1992); Rodan, G. A. et al., "Therapeutic Approaches to Bone Diseases," Science Vol 289, 1 Sep. 2000.

Another embodiment of the invention is a method of treating of preventing periodontal disease or tooth loss in a mammal in need thereof by administering to the mammal a therapeutically effective amount of any of the compounds or pharmaceutical compositions described above. The use of SERMs to treat periodontal disease or tooth loss in a mammal is known in the literature, see Rodan, G. A. et al., "Terapeutic Approaches to Bone Diseases," Science Vol 289, 1 Sep. 2000 pp. 1508–14.

Another embodiment of the invention is a method of treating of preventing Paget's disease in a mammal in need thereof by administering to the mammal a therapeutically effective amount of any of the compounds or pharmaceutical compositions described above. The use of SERMs to treat Paget's disease in a mammal is known in the literature, see Rodan, G. A. et al., "Therapeutic Approaches to Bone Diseases," Science Vol 289, 1 Sep. 2000 pp. 1508–14.

Another embodiment of the invention is a method of treating or preventing uterine fibroid disease in a mammal in need thereof by administering to the mammal a therapeutically effective amount of any of the compounds or pharmaceutical compositions described above. The use of SERMs to treat uterine fibroids, or uterine leiomyomas, is known in the literature, see Palomba, S., et al, "Effects of raloxifene treatment on uterine leiomyomas in postmenopausal women," Fertil Steril. 2001 July;76(1):38–43.

Another embodiment of the invention is a method of treating or preventing obesity in a mammal in need thereof by administering to the mammal a therapeutically effective amount of any of the compounds or pharmaceutical compositions described above. The use of SERMs to treat obesity is known in the literature, see Picard, F. et al., "Effects of the estrogen antagonist EM-652. HCl on energy balance and lipid metabolism in ovariectomized rats," Int J Obes Relat Metab Disord. 2000 July;24(7):830–40.

Another embodiment of the invention is a method of treating or preventing cartilage degeneration, rheumatoid arthritis or osteoarthritis in a mammal in need thereof by administering to the mammal a therapeutically effective amount of any of the compounds or pharmaceutical compositions described above. The use of SERMs to treat cartilage degeneration, rheumatoid arthritis or osteoarhritis is known in the literature, see Badger, A. M. et al., "Idoxifene, a novel selective estrogen receptor modulator, is effective in a rat model of adjuvant-induced arthritis." J Pharmacol Exp Ther. 1999 December;291(3):1380–6.

Another embodiment of the invention is a method of treating or preventing endometriosis in a mammal in need thereof by administering to the mammal a therapeutically effective amount of any of the compounds or pharmaceutical compositions described above. The use of SERMs to treat endometriosis is known in the art, see Steven R. Goldstein, "The Effect of SERMs on the Endometrium," Annals of the New York Academy of Sciences 949:237–242 (2001).

Another embodiment of the invention is a method of treating or preventing urinary incontinence in a mammal in need thereof by administering to the mammal a therapeutically effective amount of any of the compounds or pharmaceutical compositions described above. The use of SERMs to treat urinary incontinence is known in the art, see, Goldstein, S. R., "Raloxifene effect on frequency of surgery for pelvic floor relaxation," Obstet Gynecol. 2001 July;98(1):91–6 and Matsubara, S., et al., "Estrogen Levels Influence Beta-3-adrenoreceptor-mediated Relaxation of the Female Rat Detrusor Muscle," Urology 59: 621–625, 2002.

Another embodiment of the invention is a method of treating or preventing cardiovascular disease, restenosis, lowering levels of LDL cholesterol and inhibiting vascular smooth muscle cell proliferation in a mammal in need thereof by administering to the mammal a therapeutically effective amount of any of the compounds or pharmaceutical compositions described above. The utility of SERMs in treating or preventing cardiovascular disease, restenosis, lowering levels of LDL cholesterol and inhibiting vascular smooth muscle cell proliferation is known in the art, see Nuttall, M E et al., "Idoxifene: a novel selective estrogen receptor modulator prevents bone loss and lowers cholesterol levels in ovariectomized rats and decreases uterine weight in intact rats," Endocrinology 1998 December;139(12):522–434; Jordan, V. C. et al., "Selective estrogen receptor modulation and reduction in risk of breast cancer, osteoporosis and coronary heart disease," Natl Cancer Inst 2001 October; 93(19):1449–57; Guzzo J A., "Selective estrogen receptor modulators—a new age of estrogens in cardiovascular disease?," Clin Cardiol 2000 January;23(1): 15–7; Simoncini T, Genazzani A R., "Direct vascular effects of estrogens and selective estrogen receptor modulators," Curr Opin Obstet Gynecol 2000 June;12(3):181–7.

Another embodiment of the invention is a method of treating or preventing the impairment of cognitive functioning or cerebral degenerative disorders in a mammal in need thereof by administering to the mammal a therapeutically effective amount of any of the compounds or pharmaceutical compositions described above. The utility of SERMs to prevent the impairment of cognitive functioning is known in the art, see Yaffe, K., K. Krueger, S. Sarkar, et al. 2001, "Cognitive function in postmenopausal women treated with raloxifene," N. Eng. J. Med. 344: 1207–1213.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to estrogen functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be admninistered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an inhibitor of cholesxterol ester transfer protein; an integrin receptor antagonist; an osteoblast anabolic agent, such as PmH; calcitonin; Vitamin D or a synthetic Vitamin D analogue; an aromatase inhibitor; selective serotonin reuptake inhibitors (SSRIs); and the pharmaceutically acceptable salts and mixtures thereof. A preferred combination is a compound of the present invention and an organic bisphosphonate. Another preferred combination is a compound of the present invention and a cathepsin K inhibitor. Another preferred combination is a compound of the present invention and an estrogen. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

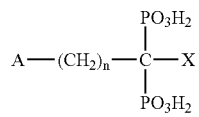

wherein n is an integer from 0 to 7 and wherein A and X are independently selected from the group consisting of H, OH, halogen, $NH_2$, SH, phenyl, C1–C30 alkyl, C3–C30 branched or cycloalkyl, bicyclic ring structure containing two or three N, C1–C30 substituted alkyl, C1–C10 alkyl substituted $NH_2$, C3–C10 branched or cycloalkyl substituted $NH_2$, C1–C10 dialilyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1–C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bis-phosphonic acid.

Alendronate (also known as alendronate sodium or alendronate monosodium trihydrate), 4-amino-1-hydroxybutyl-idene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yaamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000, µg/kg body weight and preferably about 10 to about 2000 µg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week. The bisphosphonates may also be administered monthly, ever six months, yearly or even less frequently, see WO 01/97788 (published Dec. 27, 2001) and WO 01/89494 (published Nov. 29, 2001).

"Estrogen" includes, but is not limited to naturally occurring estrogens, estradiol ($E_2$), estrone ($E_1$), and estriol ($E_3$), synthetic conjugated estrogens, oral contraceptives and sulfated estrogens. See, Gruber C J, Tschugguel W, Schneeberger C, Huber J C., "Production and actions of estrogens" N Engl J Med 2002 January 31;346(5):340–52.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Cathepsin K inhibitors" refers to compounds which interfere with the activity of the cysteine protease cathepsin K. Nonlimiting examples of cathepsin K inhibitors can be found in PCT publications WO 00/55126 to Axys Pharmaceuticals and WO 01/49288 to Merck Frosst Canada & Co. and Axys Pharmaceuticals.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163–172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HBG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

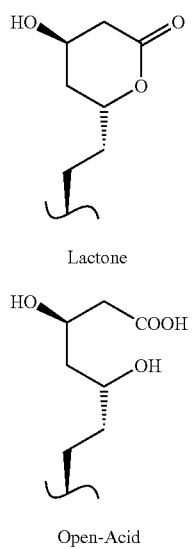

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used herein, "cholesterol ester transfer protein inhibitor" refers to an inhibitor of cholesterol ester transfer protein (CETP), a plasma protein that mediates the exchange of cholesteryl ester in high-density lipoprotein (HDL) for triglycerides in very low density lipoprotein (VLDL). A non-limiting example of a CETP inhibitor is torcetrapib.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v \beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ ($>10^7$/ osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690–709 (1993). Studies have demonstrated the clinical benefits of parathyroid hormone in stimulating bone formation and thereby increasing bone mass and strength. Results were reported by R M Neer et al., in New Eng J Med 344 1434–1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525–1531 (2001)] and may also have potential as anabolic agents for treating osteoporosis.

Calcitonin is a 32 amino acid pepetide produced primarily by the thyroid which is known to participate in calcium and phosphorus metabolism. Calcitonin suppresses resorption of bone by inhibiting the activity of osteoclasts. Thus, calcitonin can allow osteoblasts to work more effectively and build bone.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: lo-hydroxy vitamin D; 25-hydroxy vitamin D, and $1\alpha,25$-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the-kidney by cytochrome P450-monooxygenase, 25 (OH) D-1$\alpha$-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be reponsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, 3$^{rd}$ ed., 990–1013 (1995). However, elevated levels of 1$\alpha$,25-dihydroxy vitamin $D_3$ can result in an increase of calcium concentration in the blood and in the abnormal control of calcium concentration by bone metabolism, resulting in hypercalcemia. 1$\alpha$,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

As used herein, the term "aromatase inhibitor" refers to an inhibitor of aromatase, an enzyme which effects the aromatasation of ring A in the metabolic formation of various steroid hormones. Various cancers, for example breast cancer, and other disorders are dependent upon circulating steroid hormones which have an aromatic ring A. By removing the source of ring A hormones, such cancers and other disorders can be treated. Nonlimiting examples of aromatase inhibitors include anastrozole, letrozole and exemestane.

Selective Serotonin Reuptake Inhibitors act by increasing the amount of serotonin in the brain. SSRIs have been used successfully for a decade in the United States to treat depression. Non-limiting examples of SSRIs include fluoxetine, paroxetine, sertraline, citalopram, and fluvoxamine. SSRIs are also being used to treat disoreders realted to estrogen functioning, suchs as premenstrual syndrome and premenstrual dysmorphic disorder. See Sundstrom-Poromaa I, Bixo M, Bjorn I, Nordh O., "Compliance to antidepressant drug therapy for treatment of premenstrual syndrome," J Psychosom Obstet Gynaecol 2000 December;21(4):205–11.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invetion therefore encompasses the use of the instantly claimed compounds in combination with a second agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; an aromatase inhibitor; and the pharmaceutically acceptable salts and mixtures thereof.

These and other aspects of the invention will be apparent from the teachings contained herein.

Definitions

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein; refers to the process by which osteoclasts degrade bone.

The term "basic conditions," as used herein, refers to the incorporation or use of a base in the reaction medium. According to the Lowry-Bronsted definition, a base is a substance that accepts a proton; or according to the Lewis definition, a base is a substance that can furnish an electron pair to form a covalent bond. Examples of bases used herein, but are not limited to, are tertiary amine bases such as triethylamine, diisopropylethylamine, or the like.

The term "acidic conditions," as used herein, refers to the incorporation or use of an acid in the reaction medium. According to the Lowry-Bronsted definition, an acid is a substance that gives up a proton; or according to the Lewis definition, an acid is a substance that can take up an electron pair to form a covalent bond. Examples of acids used herein, but are not limited to, are strong carboxylic acids such as trifluoroacetic acid, or the like, strong sulfonic acids, such as trifluoromethane sulfonic acid, or the like, and Lewis acids, such as boron trifluoride etherate, or stannous chloride, or the like.

The term "reducing agent," as used herein, refers to a reagent capable of performing a reduction. A reduction is the conversion of a functional group or an intermediate from one category to a lower one. Examples of reducing agents used herein, but are not limited to, are triorganosilanes or stannanes, such as triethylsilane, triphenylsilane, and tri-n-butyl tin hydride, or the like. Other common reducing agents include, but are not limited to hydrogen, Raney Nickel, lithium aluminum hydride, diisobutylaluminum hydride, and the like.

The term "chemically differentiable" refers to two or more non-identical $R^6$ substituents whose unique structures are such that one of ordinary skill in the art could choose reaction conditions which would convert one of the non-identical $R^6$ substituents to H, without affecting the other $R^6$ substituent.

As used herein, "alkyl" is intended to include both branched and straight-chain saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear or branched arrangement. For example, "$C_1$–$C_{10}$ alkyl" specifically includes methyl, ethyl, propyl, butyl, pentyl, hexyl, heptyl, octyl, nonyl, decyl, and so on. "Alkoxy" represents an alkyl group of indicated number of carbon atoms attached through an oxygen bridge.

As appreciated by those of skill in the art, "halo" or "halogen" as used herein is intended to include chloro, fluoro, bromo and iodo.

The term "hydroxyalkyl" means a linear monovalent hydrocarbon raidcal of one to six carbon atoms or a branched monovalent hydrocarbon radical of three to six carbons substituted with one or two hydroxyl groups, provided that if two hydroxyl groups are present they are not both on the same carbon atom. Representative examples include, but are not limited to, hydroxymethyl, 2-hydroxyethyl, 2-hydroxypropyl, 3-hydroxypropyl, and the like.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxyl, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl substituents may be unsubstituted or unsubstituted, unless specifically defined otherwise. For example, a ($C_1$–$C_6$)alkyl may be substituted with one or more substituents selected from OH, oxo, halogen, alkoxy, dialkylamino, or heterocyclyl, such as morpholinyl, piperidinyl, and so on. In the case of a disubstituted alkyl, for instance, wherein the substituents are oxo and OH, the following are included in the definition: —(C═O)$CH_2$CH(OH)$CH_3$, —(C═O)OH, —$CH_2$(OH)$CH_2$CH(O), and so on.

The term "triorganosilyl" means those silyl groups trisubstituted by lower alkyl groups or aryl groups or combinations thereof and wherein one substituent may be a lower alkoxy group. Examples of triorganosilyl groups include trimethylsilyl, triethylsilyl, t-butyldimethylsilyl, triisopropylsilyl, triphenylsilyl, dimethylphenylsilyl, t-butyldiphenylsilyl, phenyl-t-butylmethoxysilyl and the like.

In the compounds of the present invention, alkyl, alkenyl, alkynyl, cycloalkyl, cycloalkenyl, heterocyclyl and heteroaryl groups can be further substituted by replacing one or more hydrogen atoms be alternative non-hydrogen groups. These include, but are not limited to, halo, hydroxyl, mercapto, amino, carboxy, cyano and carbamoyl.

The term "oxy" means an oxygen (0) atom. The term "thio" means a sulfur (S) atom. The term "oxo" means ═O. The term "oximino" means the ═N—O group. The term "keto" means carbonyl (C═O). The term "thiocynanto" refers to —SCN.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

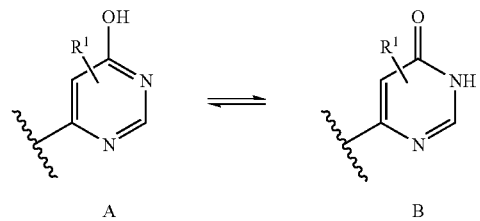

When any variable (e.g. $R^1$, $R^2$, $R^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the sub-stitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

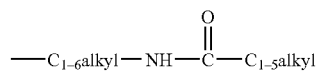

In choosing compounds of the present invention, one of ordinary skill in the art will recognize that the various substituents, i.e. $R^1$, $R^2$, $R^3$, are to be chosen in conformity with well-known principles of chemical structure connectivity.

Representative compounds of the present invention typically display submicromolar affinity for alpha and/or beta estrogen receptors. Compounds of this invention are therefore useful in treating mammals suffering from disorders related to estrogen functioning.

The compounds of the present invention are available in racemic form or as individual enantiomers. For convenience, some structures are graphically represented as a single enantiomer but, unless otherwise indicated, is meant to include both racemic and enantiomerically pure forms. Where cis and trans stereochemistry is indicated for a compound of the present invention, it should be noted that the stereochemistry should be construed as relative, unless indicated otherwise. For example, a (+) or (−) designation should be construed to represent the indicated compound with the absolute stereochemistry as shown.

Racemic mixtures can be separated into their individual enantiomers by any of a number of conventional methods. These include, but are not limited to, chiral chromatography, derivatization with a chiral auxiliary followed by separation by chromatography or crystallization, and fractional crystallization of diastereomeric salts. Deracemization procedures may also be employed, such as enantiomeric protonation of a pro-chiral intermediate anion, and the like.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1–19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The novel compounds of the present invention can be prepared according to the following general schemes, using appropriate materials, and are further exemplified by the subsequent specific examples. The compounds illustrated in the examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

For purposes of this specification, the following abbreviations have the indicated meanings:

| | | |
|---|---|---|
| Bn | = | benzyl |
| $CHCl_3$ | = | chloroform |
| $CuSO_4$ | = | copper sulfate |
| DIAD | = | diisopropylazodicarboxylate |
| DMAP | = | 4-(dimethylamino)pyridine |
| DMF | = | N,N-dimethylfonnamide |
| DMSO | = | dimethylsulfoxide |
| $Et_3N$ | = | triethylamine |
| EtOAc | = | ethyl acetate |
| EtOH | = | ethanol |
| HOAc | = | acetic acid |
| $K_2CO_3$ | = | potassium carbonate |
| MeOH | = | methanol |
| MOM | = | methoxymethyl |
| $MgSO_4$ | = | magnesium sulfate |
| $Na_2CO_3$ | = | sodium carbonate |
| $NaHCO_3$ | = | sodium bicarbonate |
| NaOH | = | sodium hydroxide |
| $Na_2SO_4$ | = | sodium sulfate |
| $NH_4Cl$ | = | ammonium chloride |
| Pd/C | = | palladium on carbon |
| $PPh_3$ | = | triphenylphosphine |
| PPA | = | polyphosphoric acid |
| PTAB | = | trimethylammoniumphenyl perbromide |
| Py | = | pyridine |
| rt | = | room temperature |
| sat. aq. | = | saturated aqueous |
| TBAF | = | Tetrabutylammonium fluoride |
| TFA | = | trifluoroacetic acid |
| THF | = | tetrahydrofuran |
| TIPS | = | triisopropyl |
| tlc | = | thin layer chromatography |
| Me | = | methyl |
| Et | = | ethyl |
| n-Pr | = | normal propyl |
| i-Pr | = | isopropyl |
| n-Bu | = | normal butyl |
| i-Bu | = | isobutyl |
| s-Bu | = | secondary butyl |
| t-Bu | = | tertiary butyl |

The compounds of the present invention can be prepared according to the following Schemes I, II, and III

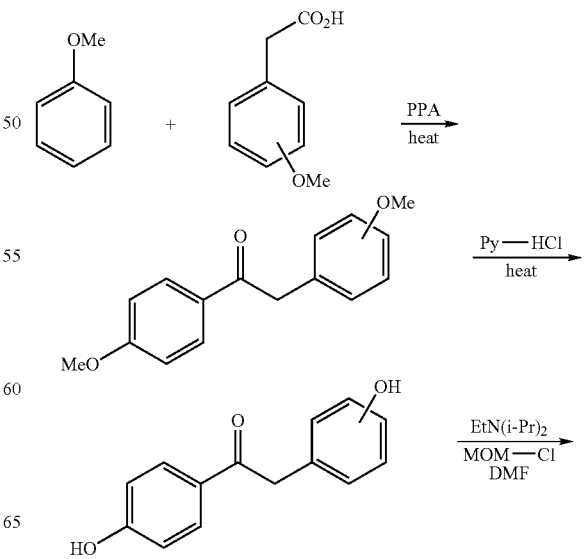

SCHEME I
Synthesis for the Preparation of Dihydro-benzoxathiins

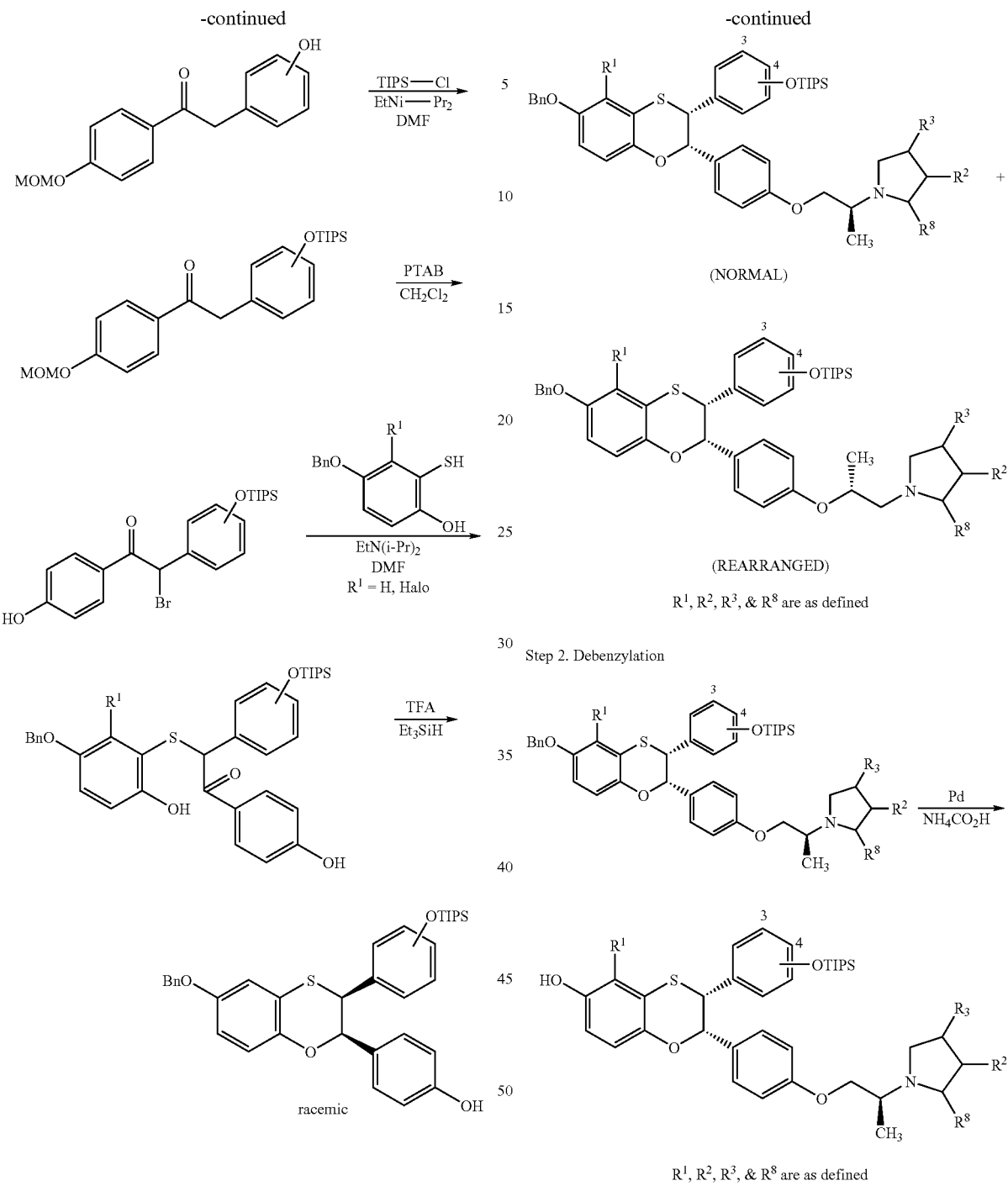
SCHEME II
Chiral Dihydro-benzoxathiin Synthesis
Step 1. Mitsunobu Reaction
Step 2. Debenzylation
Step 3. Desilylation
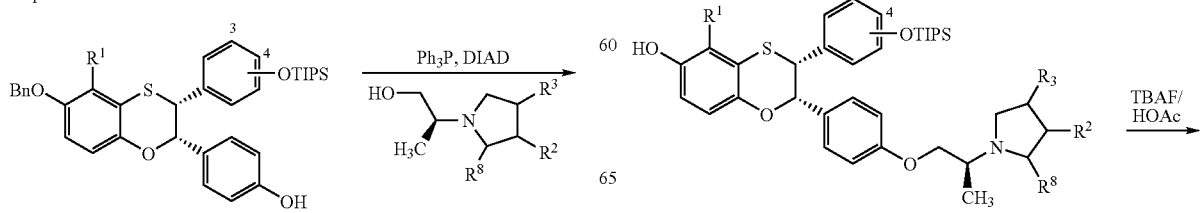

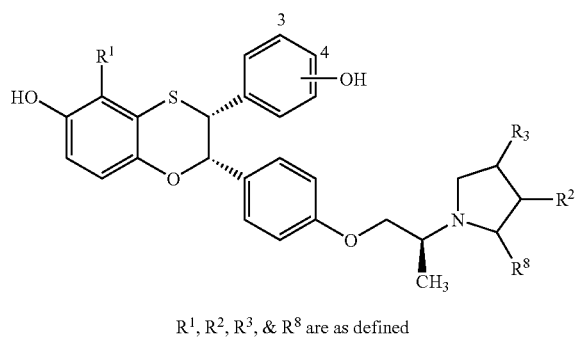

R¹, R², R³, & R⁸ are as defined

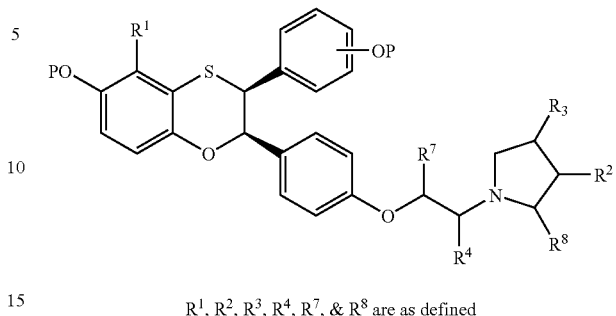

R¹, R², R³, R⁴, R⁷, & R⁸ are as defined

SCHEME III
Alternative Dihydro-benzoxathiin Synthesis

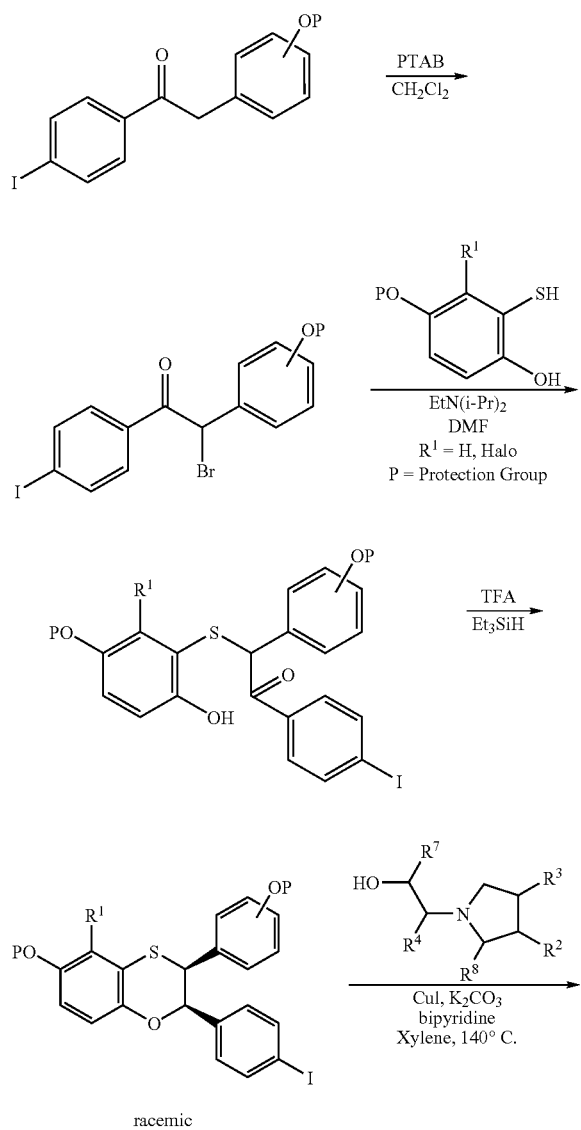

racemic

In words relative to Scheme I, an appropriately functionalized phenylacetophenone derivative, which can be prepared according to the depicted literature process, can be converted to an appropriately functionalized bromo-phenylacetophenone derivative by bromination with phenyltrimethylammonium tribromide (PTAB). In turn, the bromide can be reacted with an appropriately functionalized mercapto-phenol derivative, which can be prepared according to literature procedures, in the presence of a tertiary amine base, such as triethylamine, diisopropylethylamine, or the like, in a solvent such as dimethylformamide (DMF), formamide, acetonitrile, dimethylsulfoxide DMSO), tetrahydrofuran THF) dichloromethane, or the like, at a temperature of from −20° C. to 80° C. for as long as it takes for the reaction to complete to provide the displacement product.

This intermediate can be reductively cyclized in the presence of an organic acid such as trrifluoroacetic acid, triflic acid, or the like, or a Lewis acid such as boron trifluoride etherate, stannous chloride, or the like, and a reducing agent such as a trisubstituted silane, such triethylsilane, or the like, in a solvent such as dichloromethane, chloroform, THF, toluene, or the like at a temperature of from −40° C. to 100° C. for as long as it takes for the reaction to complete to provide the cyclized dihydro-benzoxathiin, in which the stereochemistry of the aryl substituents in the newly created ring is exclusively cis.

The alcohol intermediate can be conveniently resolved at this point by chiral chromatography into both optical antipodes. The positively rotating isomer having the (2S, 3R) absolute configuration, depicted in Scheme II, can then be reacted with a chiral pyrrolidino-ethanol derivatives such as $HOCH_2CH(CH_3)NZ_2$, or the like, wherein $NZ_2$ represents pyrrolidine, which may also be substituted, in a Mitsunobu reaction protocol, in which they are combined with a trisubstituted phosphine, such as triphenylphosphine and a diazodicarboxylate, such as diisopropylazodicarboxylate, in a suitable solvent such as THF at from 0° C. to 80° C. for as long as it takes for the reaction to complete to provide the coupled product. In addition, it should be noted that this Mitsunobu reaction proceeds through a spiro-aziridinium intermediate which typically results in the formation of two products: the "normal" addition product, and the "rearranged" product, which places the chiral center at the other carbon of the linker chain, ie, next to the oxygen atom. The variables for the Mitsunobu reaction have been well documented and are incorporated herein by reference: Mitsunobu, O. *Synthesis*, 1981, 1; Castro, B. R. *Org. React.* 1983, 29, 1; Hughes, D. L. *Org. React.* 1992, 42, 335. Finally, after the Mitsunobu reaction, the protecting groups can be sequentially removed, from either product, utilizing the appropriate method which may be found in such standard references as: Greene, T. W. and Wuts, P. G. M., *Protective Groups in Organic Synthesis*, Third Ed., Wiley, New York (1999), to give the final products of the invention. Further, it is also understood, that the foregoing chemistry can also be performed with racemic materials as well.

Alternatively, it is possible to eliminate the rearranged product depicted in Scheme II, by utilization of a different chemical process which is oulined in Scheme III. Thus, as previously described in Scheme I, an appropriately functionalized dihydrobenzoxathiin intermediate possessing an iodo group in the pendant phenyl ring can be prepared, and reacted with the selected hydroxyethylpyrrolidine derivative in a copper-catalyzed coupling reaction in a manner as described in the literature, eg. Wolter, M.; Nordmann, G.; Job, G. E.; Buchwald, S. L. *Org. Letters*, 2002, 4, 973. The unmasking of the phenolic groups can then be achieved as previously stated. Further, it is also understood, that the foregoing chemistry can also be performed with chiral materials as well.

ASSAYS

The utility of the compounds of the instant invention can be readily determined by methods well known to one of ordinary skill in the art. These methods may include, but are not limited to, the assays described in detail below. The compounds of the instant invention were tested in the following assays and found to have the relevant activity.

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ER-α or ER-β extracts are diluted 1:400 in phosphate buffered saline containing 6 mM α-monothiolglycerol. 200 μL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, 5 and 6 mM α-monothiolglycerol. To set up the assay in these receptor coated plates, add 178 ul of the same buffer to each well of the 96 well plate. Then add 20 ul of a 10 nM solution of $^3$H-estradiol to each well of the plate.

Test compounds are evaluated over a range of concentrations from 0.01 nM to 1000 nM. The test compound stock solutions should be made in 100% DMSO at 100× the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

Ovariectomized Rat Assay

In the ovariectomized (OVX) Rat Assay, estrogen-deficiency is used to induce cancellous osteopenia (e.g. low bone mineral density [BMD; mg/cm$^2$]), associated with accelerated bone resorption and formation. Both the BMD and bone resorption/formation outcomes are used to model the changes in bone that occur as women pass through menopause. The OVX Rat Assay is the principal in vivo assay used by all major academic and industrial laboratories studying the efficacy of new chemical entities in preventing estrogen-deficiency bone loss.

Sprague-Dawley female rats aged 6–8 months are OVXd and, within 24 hours, started on treatment for 42 days with vehicle or multiple doses of test compound. Untreated sham-OVX and alendronate-treated (0.003 mg/kg s.c., q.d.) or 17-β-estradiol-treated (0.004 mg/kg s.c., q.d.) groups are included as positive controls. Test compounds may be administered orally, subcutaneously, or by infusion through subcutaneously-implanted minipump. Before necropsy, in vivo dual labeling with calcein (8 mg/kg by subcutaneous injection), a bone seeking fluorochrome, is completed. At necropsy, blood, femurs, a vertebral body segment, and the uterus, are obtained.

The routine endpoints for the OVX Rat Assay include assessments of bone mass, bone resorption, and bone formation. For bone mass, the endpoint is BMD of the distal femoral metaphysis, a region that contains about 20% cancellous bone. The vertebral segment, a region with ~25% cancellous bone may also be used for BMD determination. The BMD measurement is made by dual energy x-ray absorptiometry (DXA, Hologic 4500A; Waltham, Mass.). For bone resorption, the endpoint is urinary deoxypyridinoline crosslinks, a bone collagen breakdown product (uDPD; expressed as nM DPD/nM creatinine). This measurement is made with a commercially available kit (Pyrilinks; Metra Biosystems, Mountain View, Calif.). For bone formation, the endpoints are mineralizing surface and mineral apposition rate, histomorphometric measures of osteoblast number and activity. This measurement is done on 5 μm sections of the non-decalcified proximal tibial metaphysis, using a semiautomated system (Bioquant; R&M Biometrics; Nashville, Tenn.). Similar endpoints and measuring techniques for each endpoint are commonly used in postmenopausal women.

Rat Cholesterol Lowering Assay

Sprague-Dawley rats (5 per group) weighing about 250 g were subcutaneously dosed with compounds of the present invention dissolved in propylene glycol for 4 days. A group of 5 rats was dosed with vehicle only. On the fifth day, rats were euthanized with carbon dioxide and their blood samples were obtained. Plasma levels of cholesterol were assayed from these samples with commercially available cholesterol determination kits from Sigma.

MCF-7 Estrogen Dependent Proliferation Assay

MCF-7 cells (ATCC #HTB-22) are human mammary gland adenocarcinoma cells that require estrogen for growth. The growth media (GM) for the MCF-7 cells is Minimum Essential Media (without phenol red) supplemented with fetal bovine serum (FBS) to 10%. The FBS serves as the sole source of estrogen and this GM supports the full growth of the cells and is used for the routine growth of the cell cultures. When MCF-7 cells are placed in a media in which 10% Charcoal-Dextran treated fetal bovine serum (CD-FBS) is substituted for FBS, the cells will cease to divide but will remain viable. The CD-FBS does not contain detectable levels of estrogen and the media containing this sera is referred to as Estrogen Depleted Media (EDM). The addition of estradiol to EDM stimulates the growth of the MCF-7 cells in a dose dependent manner with an $EC_{50}$ of 2 pM.

Growing MCF-7 cells are washed several times with EDM and the cultures then maintained in EDM for a minimum of 6 days in order to deplete the cells of endogenous estrogen. On day 0 (at the startof the assay), these estrogen depleted cells are plated into 96-well cell culture plates at a density of 1000 cells/well in EDM in a volume of 180 ul/well. On day 1 test compounds are diluted in a 10-fold dilution series in EDM and 20 ul of these dilutions added to the 180 ul of media in the appropriate well of the cell plate resulting in a further 1:10 dilution of the test compounds. On days 4 and 7 of the assay, the culture supernatant is aspirated and replaced with fresh EDM and test compound dilutions as above. The assay is terminated at day 8–10 when the appropriate controls reach 80–90% confluency. At this point, the culture supernatants are aspirated, the cells washed 2× with PBS, the wash solution aspirated and the protein content of each well determined. Each drug dilution is evaluated on a minimum of 5 wells and the range of dilution of the test compounds in the assay is 0.001 nM to 1000 nM. The assay in the above format is employed to determine the estradiol agonist potential of a test compound.

In order to evaluate the antagonist activity of a test compound, the MCF-7 cells are maintained in EDM for a minimum of 6 days. Then on day 0 (at the start of the assay), these estrogen depleted cells are plated into 96-well cell culture plates at a density of 1000 cells/well in EDM in a volume of 180 ul/well. On day 1 the test compounds in fresh media containing 3 pM estradiol are applied to the cells. On days 4 and 7 of the assay, the culture supernatant is aspirated and replaced with fresh EDM containing 3 pM estradiol and the test compound. The assay is terminated at day 8–10 when the appropriate controls reach 80–90% confluency and the protein content of each well is determined as above.

Rat Endometriosis Model

Animals:
Species: *Rattus norvegicus*
Strain: Sprague-Dawley CD
Supplier: Charles River Laboratories, Raleigh, N.C.
Sex: Female Weight: 200–240 gram Rats are single-housed in polycarbonate cages and are provided Teklad Global Diet 2016 (Madison, Wis.) and bottled reverse osmosis purified H2O ad libitum. They are maintained on a 12/12 light/dark cycle.

Rats are anesthetized with Telazo™ (20 mg/kg, ip) and oxymorphone (0.2 mg/kg sc) and positioned dorsoventrally on a sterile drape. Body temperature is maintained using a underlying circulating water blanket. The surgical sites are shaved with clippers and cleaned using three cycles of betadine/isopropyl alcohol or Duraprep® (3M). The incisional area is covered with a sterile drape.

Using aseptic technique, a 5 cm midline lower abdominal incision is made through the skin, subcutaneous and muscle layers. A bilateral ovariectomy is performed. The left uterine blood vessels are ligated and a 7 mm segment of the left uterine horn is excised. The uterus is closed with 4-0 gut suture. The myometrium is aseptically separated from the endometrium and trimmed to 5×5 mm. The trimmed section of the endometrium is transplanted to the ventral peritoneal wall with the epithelial lining of the segment opposed to the peritoneal wall. The explanted endometrial tissue is sutured at its four corners to the body wall using sterile 6-0 silk. The abdominal muscular layer is closed using sterile 4-0 chromic gut. The skin incision is closed using sterile stainless surgical clips. A sterile 90-day sustained release estrogen pellet (Innovative Research of America, 0.72 ng/pellet; circulating estrogen equivalent of 200–250 pg/mL) is implanted subcutaneously in the dorsal lateral scapular area. A sterile implantable programmable temperature transponder (RPTM) (BMDS, Seaford, Del.) is injected subcutaneously in the dorsoscapular region. The rats are observed until fully ambulatory, and allowed to recover from surgery undisturbed for 3 weeks.

Three weeks after transplantation of the endometrial tissue, the animals undergo a repeat laparotomy using aseptic surgical site preparation and technique. The explant is evaluated for graft acceptance, and the area is measured with calipers and recorded. The animals with rejected grafts are removed from the study. Animals are sorted to create similar average explant volume per group.

Drug or vehicle(control) treatment is initiated one day after the second laparotomy and continued for 14 days. Body temperature is recorded every other day at 10:00 am using the BMDS scanner.

At the end of the 14 day treatment period, the animals are euthanized by $CO_2$ overdose. Blood is collected by cardiocentesis for circulating estrogen levels. The abdomen is opened, the explant is examined, measured, excised, and wet weight is recorded. The right uterine horn is excised, and wet and dry weights are recorded.

EXAMPLES

Example 1

Preparation of 4-benzyloxy-2-mercapto-phenol

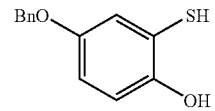

Step A:
To a solution of thiourea (26.66 g, 0.35 moles) in 2 N hydrochloric acid (350 mL) was added a solution of 1,4-benzoquinone (25.04 g, 0.23 moles) in acetic acid (350 mL) via a dropping funnel. The resulting amber solution was stirred at ambient temperature for 35 min., then heated to 110° C. for 3 h under nitrogen. The reaction was cooled in an ice bath at which time, a pale lavender solid precipitated out of solution. The resulting mixture was stored at 0° C. for 16 h. The precipitate was collected by vacuum filtration and redissolved in ethyl acetate. The ethyl acetate solution was washed with brine, dried over sodium sulfate, and concentrated in vacuo to give the desired product as a pale lavender solid. $^1$H NMR (500 MHz, $CDCl_3$) δ (ppm): 5.05 (bs, 1H), 6.80 (dd, 1H), 6.93 (d, 1H), 7.19 (d, 1H).

Step B:
To a solution of the thiocarbonate from Step A (17.47 g, 0.10 moles) in anhydrous DMF (200 mL) at 0° C. was added cesium carbonate (54.30 g, 0.16 moles) under nitrogen followed by benzyl bromide (14.8 mL, 0.12 moles). The reaction became a dark green mixture. After 1 h, approximately 10–20% of the starting material remained. The reaction was allowed to stir for an additional 1 h, before partitioning the reaction between ethyl acetate and ice water.

The organic layer was collected, washed with water and brine, dried over sodium sulfate, and concentrated in vacuo to afford a dark brown oil. The residue was purified by silica gel chromatography with 10% ethyl acetate in hexanes as the eluant to give the desired product as a white solid. $^1$H NMR (500 MHz, CDCl$_3$) δ (ppm): 5.08 (s, 2H), 6.95 (dd, 1H), 7.02 (d, 1H), 7.21 (d, 1H), 7.36–7.43 (m, 5H).

Step C:

A solution of the protected thiocarbonate (15.10 g, 59 mmol) from Step B in 100 mL of tetrahydrofuran and 50 mL of ethanol was sparged with nitrogen for 20 min. before adding 5 N sodium hydroxide (47 mL, 233 mmol). The reaction was stirred at ambient temperature with continuous nitrogen bubbling. After 1 h, the reaction was cooled to 0° C. and 2 N hydrochloric acid (116 mL, 233 mmol) was added. The resulting pale green reaction mixture was extracted with ethyl acetate. The organic layer was collected, washed with brine, dried over sodium sulfate, and concentrated in vacuo to give a pale green/yellow solid. $^1$H NMR (500 MHz, CD$_3$OD) δ (ppm): 4.9 (s, 2H), 688 (d, 1H), 6.96 (d, 1H), 7.04 (dd, 1H), 7.3–7.4 (m, 5H)

Example 2

Preparation of 2-fluoro-3-mercapto-hydroquinone

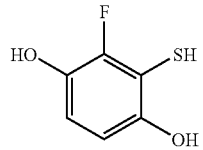

Step A:

A 3-neck 1-liter flask equipped with a low temperature thermometer, N$_2$ line, and dropping funnel was charged with 1,4-dimethoxy-2-fluorobenzene (20.42 g, 131 mmol). The solid was dissolved in distilled TBF (450 mL) and cooled to an internal temperature of −74° C. A 2.5 M solution of n-BuLi in hexane (63 mL, 157 mmol) was subsequently added over 25 min. under N$_2$ via a dropping funnel. The reaction was maintained at −75° C. for 30 min., before adding solid sulfur (5.01 g, 157 mmol) in one portion. Nitrogen sparging of the reaction mixture was begun at this time and continued throughout the reaction. The internal temperature rose to −65° C. but quickly recooled to −75° C. The reaction temperature was maintained at −75° C. for 30 min. At this time, the excess dry ice in the dry ice/acetone bath was removed and the reaction was allowed to slowly warm to −20° C. over 1.5 h. The reaction was quenched with 2 N HCl with vigorous N$_2$ bubbling until the color of the reaction turned pale yellow. The internal temperature of the reaction rose to 10° C. The reaction was extracted with EtOAc. The organic layer was collected, washed with brine, dried over MgSO$_4$, filtered, and concentrated in vacuo. The yellow residue was purified by silica gel chromatography with 20% EtOAc/hexane as the eluant to give the desired product as a light yellow solid. $^1$H 600 MHz NMR(CDCl$_3$) ppm(δ): 3.84 (s, 3H), 3.86 (s, 3H), 6.56 (dd, J=1.8 Hz, J=8.9 Hz, 1H), 6.70 (t, 1H).

Step B:

To a solution of the thiophenol (10.66 g, 57 mmol) generated in Step A in CH$_2$Cl$_2$ (100 mL) at 0° C. under N$_2$ was added a 1 M solution of BBr$_3$ in CH$_2$Cl$_2$ (227 mL, 227 mmol) via a dropping funnel over 10 min. The reaction solution was continuously sparged with N$_2$. After stirring at 0° C. for 1 h, the reaction was quenched slowly with cold 2 N HCl. The resulting mixture was extracted with EtOAc. The organic layer was collected, washed with brine, dried over Na$_2$SO$_4$, filtered, and concentrated in vacuo. The resulting light purple solid was used without further purification. $^1$H 600 MHz NMR(CD$_3$OD) ppm(δ): 6.42 (dd, J=1.8 Hz, J=8.9 Hz, 1H), 6.51 (t, 1H).

Example 2A

Preparation of

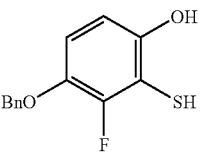

Step A: To a solution of the crude fluoromercaptan (12 mmol) from Example 2 in anhydrous THF (25 mL) was added 1,1'-carbonyldiimidazole (3.9 g, 24 mmol) at ambient temperature with nitrogen sparging, followed by a catalytic amount of DMAP. The reaction was stirred for 10 min., then partitioned between ethyl acetate and ice/2 N HCl. The organic layer was collected, washed with brine, dried over sodium sulfate, and concentrated in vacuo to give a pale yellow solid. Purification by silica gel chromatography with 15% ethyl acetate/hexane as the eluant afforded the desired product as a white solid (1.91 g, 83%). $^1$H 500 MHz NMR(CDCl$_3$) ppm(δ): 7.00–7.02 (m, 2H).

Step B: To a solution of the material obtained from Step A (1.91 g, 10 mmol) in anhydrous DMF (20 mL), was added cesium carbonate (6.7 g, 21 mmol) at 0° C. under nitrogen followed by benzyl bromide (1.5 mL, 12 mmol). After 2.5 h of vigorous stirring, the reaction was filtered to remove the cesium carbonate. The filtrate was partitioned between ethyl acetate and 2 N HCl/ice. The organic layer was further washed with brine, dried over sodium sulfate, and concentrated in vacuo. Purification by silica gel chromatography with 15% ethyl acetate/hexane as the eluant gave the desired product (1.1709 g, 42%). $^1$H 500 MHz NMR(CDCl$_3$) ppm (δ): 5.19 (s, 2H), 7.00–7.02 (m, 2H), 7.36–7.44 (m, 5H).

Step C: Utilizing the procedure outlined in Example 1, Step C, the thiocarbonate (1.1709 g, 4.2 mmol) was converted to the free thiol. The crude material was used without further

Example 3

Preparation of 2-(3-methoxy-phenyl)-4-methoxy-aceptophenone

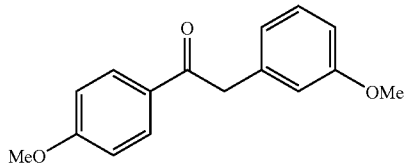

Following the procedure described in E. Napolitano, et al., *Gazz. Chim. Italia*, 1988, 118, 101, a mixture of anisole (70 g, 0.64 mol), 3-methoxyphenyl acetic acid (100 g, 0.6 mol), and 2 kg of PPA was mechanically stirred at 75° C. for 75 minutes under an atmosphere of nitrogen. The cooled, red reaction mixture was poured slowly into ice-water and then extracted with several portions of ethyl acetate. The combined extracts were washed with saturated sodium bicarbonate solution and brine, dried over anhydrous sodium sulfate, filtered, and the solvent removed in vacuo to give the crude product which was used without further purification. The material may be purified by column chromatography (Biotage) using hexanes-methylene chloride (2:1) as eluant. $^1$H 500 MHz NMR(CDCl$_3$) ppm(δ): 3.81 (s, 3H), 3.89 (s, 3H), 4.23 (s, 2H), 6.84 (dd, 1H), 6.88 (d, 1H), 6.89 (d, 1H), 6.95 (d, 2H), 7.26 (t, 1H), and 8.02 (d, 2H).

Example 4

Preparation of 2-(3-hydroxy-phenyl)-4-hydroxy-acetophenone

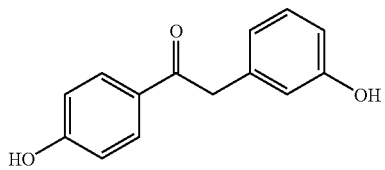

A mixture of 2-(3-methoxyphenyl)-4-methoxy-acetophenone (148.4 g, 0.6 mol), generated in Example 3, and pyridine-HCl (460 g, 3.98 mol) was heated to 184° C. under N$_2$ for 3.5 h. After this time, an additional 11 g of pyridine hydrochloride was added and the mixture and heated further for 1.8 h. Another 12.5 g of pyridine hydrochloride was added and after another 1.5 h, the reaction was cooled in an ice bath and ice/H$_2$O was added. The resulting mixture was extracted with EtOAc. The organic extract was washed with 2 N HCl and brine, dried over Na$_2$SO$_4$, and concentrated in vacuo. The resulting brown residue was purified by silica gel chromatography (Biotage) with 40% EtOAc/hexane as the eluant to afford the desired product as a yellow solid, and the mono-methoxy product which could be recycled; $^1$H 500 MHz NMR(d$_6$-acetone) ppm(δ): 4.18 (s, 2H), 6.69 (dd, 1H), 6.78 (m, 2H), 6.91 (d, 2H), 7.1 (t, 1H), and 7.97 (d, 2H).

Example 5

Protecting Group Procedures for Phenyl-acetophenone Derivatives

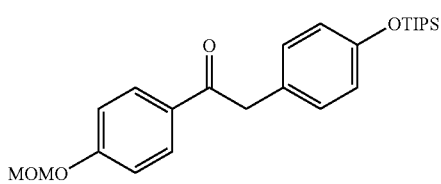

Preparation of 4'-methoxymethyloxy-2-(4-triisopropylsilyloxy-phenyl)acetophenone (5a)

Step A:

To a stirred solution of 3.0 g (13.2 mmol) of dry 4,4'-dihydroxy-desoxybenzoin (prepared as described by Poirier, D., etal, *J. Med. Chem.*, 1994, 37, 1115; and freshly azeotroped with toluene) in 25 mL of DMF at 0° C. was added 5.7 mL (5.7 mmol) of neat diisopropylethylamine. To this stirred solution was added slowly 1.25 mL (19.73 mmol) of chloromethylmethylether (MOMCl). The ice-water bath was removed and the mixture was stirred further under an atmosphere of nitrogen for 18 hours. The mixture was then poured into a saturated NaHCO$_3$ solution, extracted with EtOAc, and the extract washed with water, and dried over anhydrous MgSO$_4$. After evaporation of the solvent, the residue was purified by silica gel chromatography (EtOAc/Hexane=1:1) to provide the product, as a solid. $^1$H NMR (400 MHz, CDCl$_3$) δ (ppm): 8.0 (d, 2H), 7.19(d, 2H), 7.10 (d, 2H), 6.8 (d, 2H), 5.23 (s, 2H), 4.8 (s, 1H), 4.2 (s, 2H), 3.5 (s, 3H).

Step B:

To a stirred solution of the product obtained from Step A (423 mg, 1.55 mmol) and imidazole (211 mg, 3.1 mmol) in 20 mL of dry DMF at 0° C. was added triisopropylsilyl chloride [TIPS-Cl] (3.1 mmol) and the reaction mixture was allowed to warm to room temperature and stirred further for 2–3 hours. The reaction was quenched by the addition of aqueous NaHCO$_3$ solution and extracted with EtOAc. The organic layer was washed with brine and dried with MgSO$_4$. Chromatography (10% EtOAc/hexane) yielded the desired product. $^1$H NMR (400 MHz, CDCl$_3$) δ (ppm): 8.0 (d, 2H), 7.12 (d, 2H), 7.08 (d, 2H). 6.82 (d, 2H), 5.21 (s, 2H), 4.18 (s, 2H), 3.5 (s, 3H), 1.24 (m, 3H), 1.1 (d, 18H).

Utilizing one or both of the foregoing experimental steps the following compounds were prepared:

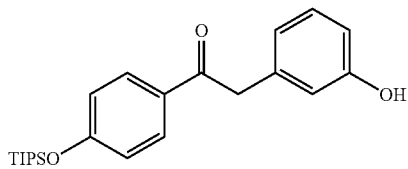

5b. 2-(3-hydroxy-phenyl)-4-triisopropyloxy-acetophenone.

Using the ketone (8.7 g, 38 mmol) from Example 4 in anhydrous DMF (140 mL) at 0° C. under N$_2$ was added Hunig's base (8.0 mL, 46 mmol) followed by dropwise addition of TIPSCl (9.0 mL, 42 mmol). After stirring for 25 min. at 0° C., the reaction was partitioned between ice/2N HCl and EtOAc. The organic layer was collected, washed with brine, dried over Na$_2$SO$_4$, filtered, and concentrated in vacuo to give an oil. The residue was purified by silica gel chromatography with 20% EtOAc/hexane as the eluant to give the desired product as a yellow solid. $^1$H 500 MHz NMR(CDCl$_3$) ppm(δ): 1.13 (d, 18H), 1.30 (m, 3H), 4.20 (s, 2H), 6.77–6.82 (m, 3H), 6.91 (d, 2H), 7.20 (t, 1H), 7.99 (d, 2H).

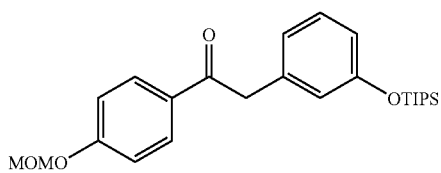

5c. 4'-methoxymethyloxy-2-(3-triisopropylsilyloxy-phenyl)-acetophenone.

Using the material from Example 4 and final chromatography (hexanes-ethyl acetate, 85:15) gave the product. $^1$H 500 MHz NMR(CDCl$_3$) ppm(δ): 1.07 (d, 18H), 1.2 (m, 3H), 3.5 (s, 3H), 4.19 (s, 2H), and 5.22 (s, 2H).

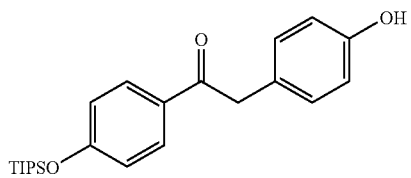

5d. 2-(4-hydroxy-phenyl)-4-triisopropyloxy-acetophenone.

Utilizing the material from Example 4, 2-(4-hydroxyphenyl)-1-{4-[(triisopropylsilyl)oxy]phenyl}ethanone was prepared. $^1$H NMR (500 MHz, CDCl$_3$) δ (ppm): 1.17 (d, 18H), 1.32 (m, 3H), 4.20 (s, 2H), 6.80 (d, 2H), 6.94 (d, 2H), 7.18 (d, 2H), 7.99 (d, 2H).

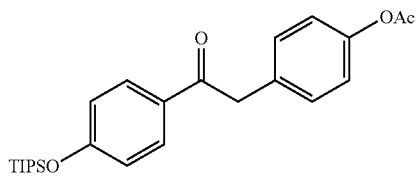

5e. 2-(4-acetoxy-phenyl)-triisopropyloxy-acetophenone.

To a solution of 10.67 g (27.7 mmol) of ketone 5d, from Example 5, in methylene chloride (150 mL) at 0° C. was added Hunig's base (6.3 mL, 36.1 mmol), DMAP (1.01 g, 8.3 mmol), and acetyl chloride (2.4 mL, 33.3 mmol) in that order under an atmosphere of nitrogen. After stirring for 25 min., the reaction was partitioned between ethyl acetate and ice/2 N HCl. The organic layer was collected, washed with water and brine, and dried over sodium sulfate. Concentration in vacuo afforded the desired prodcut as an orange solid. The solid was azeotroped with toluene and used without further purification. $^1$H NMR (600 MHz, CDCl$_3$) δ (ppm): 1.10 (d, 18H), 1.26 (m, 3H), 2.29 (s, 3H), 4.21 (s, 2H), 6.90 (d, 2H), 7.04 (d, 2H), 7.27 (d, 2H), 7.98 (d, 2H).

Example 6

Bromination Procedure of Phenyl-acetophenone Derivatives

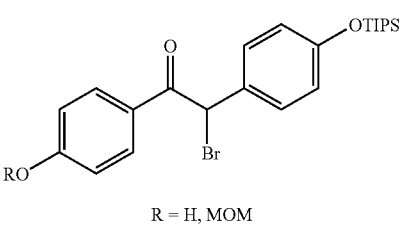

R = H, MOM

Preparation of 4'-methoxymethyloxy- and 4'-hydroxy-2-bromo-2-(4-triisopropyloxy-phenyl)-acetophenones (6a,b)

To a stirred solution of 0.5 g (1.16 mmol) of the product from Step B of Example 5 in 100 mL of anhydrous THF was added 0.39 g (1.16 mmol) of trimethylphenylammonium perbromide (PTAB) at 0° C. The ice-water bath was removed, and the mixture was stirred further for one hour. The solution was then filtered and washed with water and brine and dried over MgSO$_4$. Removal of the solvent afforded the mixture of bromo-ketones (the MOM group was partially removed), which was used without further purification.

6a. Bromoketone with MOM Group:

$^1$H NMR (400 MHz, CDCl$_3$) δ (ppm): 8.0 (d, 2H), 7.4 (d, 2H), 6.88 (d, 2H), 6.86 (d, 2H), 6.36 (s, 1H), 1.24 (m, 3H), 1.1 (d, 18H);

6b. Bromoketone Without MOM Group:

$^1$H NMR (400 MHz, CDCl$_3$) δ (ppm): 7.94 (d, 2H), 7.4 (d, 2H), 6.88 (d, 2H), 6.86 (d, 2H), 6.36 (s, 1H), 1.24 (m, 3H), 1.1 (d, 18H).

Alternatively, after the mixture was stirred for one hour, a few drops of 48% HBr was added to the mixture and it was stirred further until a thin layer chromatogram indicated that the removal of the methoxymethyl (MOM) group was complete, thus yielding only 4'-hydroxy-2-bromo-2-(4-triisopropylsilyloxy-phenyl)-acetophenone 6b.

6c. Preparation of 4'-hydroxy-2-(3-triisopropylsilyloxy-phenyl)-acetophenone.

To a stirred solution of 40.7 g (0.095 mol) of 4'-methoxymethyloxy-2-(3-triisopropylsilyloxy-phenyl)-acetophenone (5c), from Example 5, in 400 mL of dichloromethane at 0° C. was added all at once 37.5 g (0.099 mol) of solid trimethylammoniumphenyl perbromide. The ice-water bath was removed and the reaction mixture was stirred further for 4 h under an inert atmosphere of nitrogen. The reaction mixture was partitioned between ethyl acetate, ice, brine, 5% aqueous sodium thiosulfate, and saturated sodium bicarbonate. The organic phase was separated washed with brine; dried over anhydrous sodium sulfate, filtered, evaporated, and dried in vacuo to give the crude product which was used without further purification. $^1$H 500 MHz NMR(CDCl$_3$) ppm(δ): 1.07 (d, 18H), 1.2 (m, 3H), and 6.3 (s, 1H).

Using the foregoing procedures the following compound was prepared:

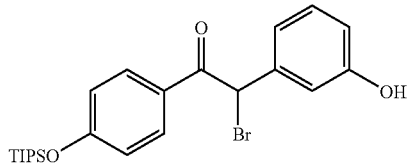

6d. 4-triisopropylsilyloxy-2-bromo-2-(3-hydroxyphenyl)-acetophenone.

Using 8.93 g (23 mmol) of 4-triisopropylsilyloxy-2-(3-hydroxyphenyl)-acetophenone (5b) from Example 5, crude 4-triisopropylsilyloxy-2-bromo-2-(3-hydroxyphenyl)-acetophenone was realized which was used without further purification. $^1$H 500 MHz NMR(CDCl$_3$) ppm($\delta$): 1.10 (d, 18H), 1.25 (m, 3H), 6.29 (s, 1H), 6.80–7.22 (m, 6H), 7.90 (d, 2H);

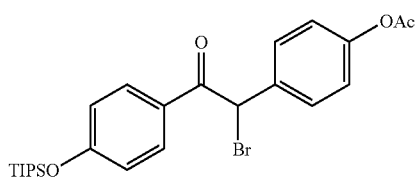

6e. 4-triisopropylsilyloxy-2-bromo-2-(3-acetoxyphenyl)-acetophenone.

Using the ketone 5e, prepared in Example 5, the desired product was obtained as an orange oil and was used without further purification. $^1$H NMR (500 MHz, CDCl$_3$) $\delta$ (ppm): 1.10 (d, 18H), 1.28 (m, 3H), 2.29 (s, 3H), 6.35 (s, 1H), 6.90 (d, 2H), 7.12 (d, 2H), 7.59 (d, 2H), 7.98 (d, 2H).

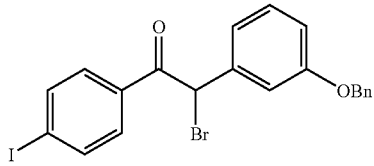

6f. 4-iodo-2-bromo-2-(3-benzyloxyphenyl)-acetophenone.

Utilizing the ketone (1.82 g, 4.2 mmol), prepared by the reaction of 3-benzyloxybenzylmagnesium chloride and Weinreb amide of p-iodobenzoic acid, the desired product was obtained as a colorless oil and was used without further purification. $^1$H 500 MHz NMR(CDCl$_3$) ppm($\delta$): 5.09 (s, 2H), 6.25 (s, 1H), 6.99 (dd, 1H), 7.23–7.36 (m, 2H), 7.30–7.43 (m, 6H), 7.69 (d, 2H), 7.81 (d, 2H).

Example 7

Preparation of Thioketones

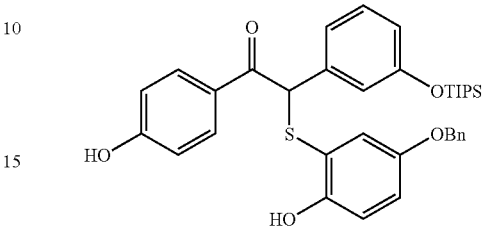

Preparation of 2-(2-hydroxy-5-benzyloxyphenylthio)-2-(3-triisopropylsilyloxy-phenyl)-4-hydroxy-acetophenone (7a).

To a stirred solution of a mixture of 23.2 g (0.099 mole) of 2-hydroxy-5-benzyloxythiophenol and 13.5 g (0.1 mole) of diisopropylethylamine in 50 mL of sieve dried DMF at 0° C. under an inert atmosphere of nitrogen was added dropwise a solution of ~0.095 mole of crude 2-bromo-2-(3-hydroxy-phenyl)-4-methoxymethyloxy-acetophenone (6c), from Example 6, in 150 mL of sieve dried DMF over 15 minutes. The resulting reaction mixture was stirred further for 3 h and then partitioned between 2N HCl/ice/water and ethyl acetate. The ethyl acetate extract was washed thrice with water and finally with brine; dried over anhydrous sodium sulfate, filtered, evaporated, and dried in vacuo to give the crude product, which was used without further purification.

$^1$H 500 MHz NMR(CDCl$_3$) ppm($\delta$): 1.07 (d, 18H), 1.2 (m, 3H), 4.84 (s, 2H), and 5.6 (s, 1H).

Utilizing the above procedure the following compounds were prepared:

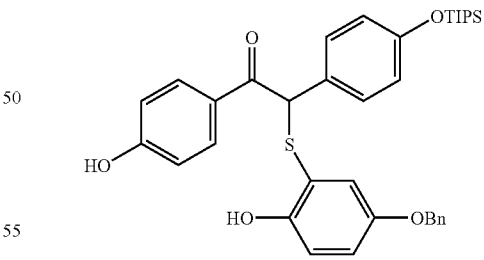

7b. 2-(2-hydroxy-5-benzyloxyphenylthio)-2-(4-triisopropylsilyloxy-phenyl)-4-hydroxy-acetophenone.

Using the bromoketone 6b from Example 6 and the mercaptan from Example 1, the desired product was obtained after silica gel chromatography using EtOAc/hexane (1:5) as the eluant. $^1$H NMR (500 MHz, acetone-d$_6$) $\delta$ (ppm): 7.95 (d, 2H), 7.40 (m, 5H), 7.20 (d, 2H), 6.80 (m, 7H), 6.20 (s, 1H), 4.85 (s, 2H), 1.23 (m, 3H), 1.10 (m, 18H); MS m/z 616 (W$^+$+1).

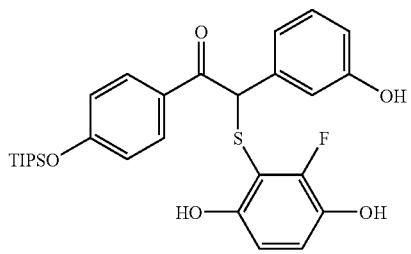

7c. 2-(2,5-dihydroxy-6-fluoro-phenylthio)-2-(3-hydroxy-phenyl)-4-triisopropylsilyloxy-acetophenone.

Using a solution of the crude thiol (13.31 g, 83 mmol) from Example 2 and the crude bromoketone 6d (64 mmol) prepared in Example 6, the desired product was obtained as a yellow foam after silica gel chromatography with 30% EtOAc/hexane as the eluant.

$^1$H 500 MHz NMR(CDCl$_3$) ppm($\delta$): 1.09 (d, 18H), 1.28 (m, 3H), 4.65 (bd, 1H), 4.91 (bs, 1H), 5.78 (s, 1H), 6.67–7.17 (m, 8H), 7.69 (s, 1H), 7.82 (d, 2H).

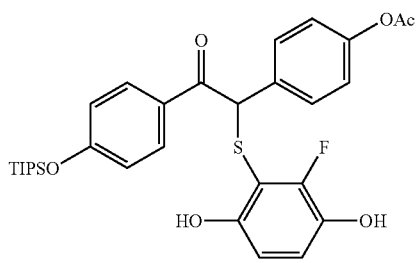

7d. 2-(2,5-dihydroxy-6-fluoro-phenylthio)-2-(3-acetoxy-phenyl)-4-triisopropylsilyloxy-acetophenone.

Using a solution of the crude thiol from Example 2 and the crude bromoketone 6e, prepared in Example 6, the desired coupled product was obtained. $^1$H NMR (500 MHz, CDCl$_3$) $\delta$ (ppm): 1.08 (d, 18H), 1.27 (m, 3H), 2.28 (s, 3H), 5.83 (s, 1H), 6.68 (d, 1H), 6.80 (d, 2H), 6.93 (t, 1H), 6.94 (d, 2H), 7.15 (d, 2H), 7.82 (d, 2H).

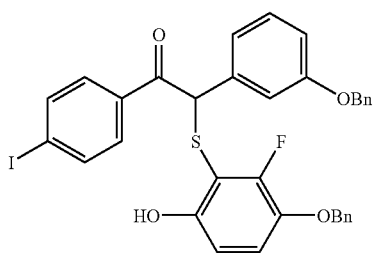

7e. 2-(2-hydroxy-5-benzyloxy-6-fluoro-phenylthio)-2-(3-acetoxy-phenyl)-4-triisopropylsilyloxy-acetophenone.

Using a solution of the crude thiol from Example 2 and the crude bromoketone 6f, prepared in Example 6, the desired coupled product was obtained after silica gel chromatography with 15% ethyl acetate/hexane as the eluant. $^1$H NMR (500 MHz, CDCl$_3$) $\delta$ (ppm): 4.95–4.99 (m, 4H), 5.76 (s, 1H), 6.63 (dd, 1H), 6.79–6.88 (m, 3H), 6.94 (t, 1H), 7.19 (t, 1H), 7.32–7.41 (m, 10H), 7.54 (d, 2H), 7.71 (d, 2H).

Example 8

General Procedure for the Formation of Dihydro-benzoxathiins

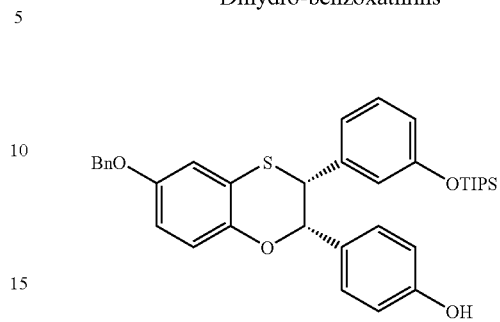

Preparation of (+)-4-((2S,3R)-6-(benzyloxy)-3-{3-[(triisopropylsilyl)oxy]phenyl}-2,3-dihydro-1,4-benzoxathiin-2-yl)phenol (8a)

To a stirred solution of ~97 mmol of crude 2-(2-hydroxy-5-benzyloxyphenylthio)-2-(3-tri-isopropylsilyloxyphenyl)-4-hydroxy-acetophenone (7a), prepared in Example 7, in 400 mL of dichloromethane at 0° C. was added 111 g (970 mmol) of neat trifluoroacetic acid (TFA) under an inert atmosphere of nitrogen. To this stirred mixture at 0° C. was added dropwise 34 g (291 mmol) of neat triethylsilane (TES) and after stirring for ~2 hour an additional 20 mL of TES was added to drive the reaction to completion. The mixture was then stirred further for 2 h. The reaction was confirmed to be complete by working up an aliquot and examining the proton NMR of the residue. The reaction mixture was partitioned between ethyl acetate/brine/ice/saturated sodium bicarbonate solution and the organic phase was separated, washed again with saturated sodium bicarbonate and finally with brine, dried over anhydrous sodium sulfate, filtered, and evaporated.

Purification by silica gel chromatography (Biotage) using hexanes-ethyl acetate (85:15) gave the product as a yellow oil;

$^1$H 500 MHz NMR(CDCl$_3$) ppm($\delta$): 1.07 (d, 18H), 1.2 (m, 3H), 4.29 (d, 1H), 5.05 (s, 2H), and 5.49 (d, 1H).

The positively rotating enantiomer was obtained via chiral chromatography on a Chiralpak® AD™ 4.6×250 mm column, available from Daicel Chemical Industries, Ltd., using heptane-isopropanol (85:15) as eluant @ 1 ml/min; retention time=5.2 min; [α]$_D$=+240.5° (c=1.045, MeOH).

Utilizing the above procedure the following compounds were prepared:

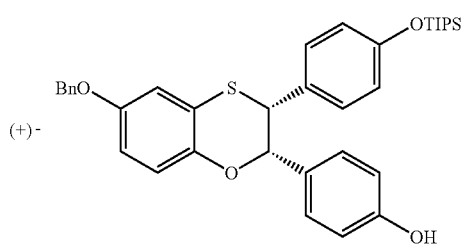

8b. 4-((2S,3R)-6-(benzyloxy)-3-{4-[(triisopropylsilyl)oxy]phenyl}-2,3-dihydro-1,4-benzoxathiin-2-yl)phenol.

Using the thioketone 7b, from Example 7, the desired product was obtained after purification by silica gel chromatography using 5% EtOAc/hexane as the eluant. $^1$H NMR (500 MHz, CDCl$_3$) δ (ppm): 7.5–7.3 (m, 5H), 6.94 (d, 1H), 6.85 (d, 2H), 6.80 (d, 2H), 6.74 (dd, 2H), 6.65(m, 4H), 5.43 (d, J=2.1 Hz, 1H), 5.05 (d, 2H), 4.30 (d, J=2.1 Hz, 1H), 1.23 (m, 3H), 1.10 (d, 18H).

Each enantiomer of the racemic dihydrobenzoxathiin was obtained via chiral chromatography using a Chiralpak® AD™ column, available from Daicel Chemical Industries, Ltd., with 30% isopropanol in hexane as the eluant; the desired fast moving isomer: $[α]_D$=+184.4° (c=0.725, MeOH); and the slow moving isomer: $[α]_D$=−188.5° (c=0.74, MeOH).

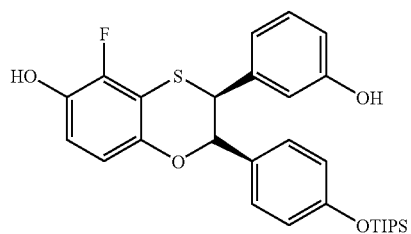

8c. 5-fluoro-3-(3-hydroxyphenyl)-2-{4-[triisopropylsilyl)oxy]phenyl}-2,3-dihydro-1,4-benzoxathiin-6-ol.

Using the thioketone 7c, from Example 7, the expected diol was realized as an off-white foam, after purification by silica gel chromatography with 30% EtOAc/hexane as the eluant.

$^1$H 500 MHz NMR(CDCl$_3$) ppm(δ): 1.11 (d, 18H), 1.25 (m, 3H), 4.33 (d, J=2.3 Hz, 1H), 5.42 (d, J=2.1 Hz, 1H), 6.38–6.97 (m, 10H).

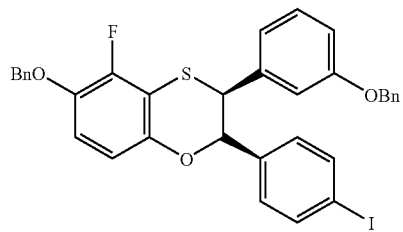

8d. 5-fluoro-6-(benzyloxy)-3-[3-(benzyloxy)phenyl]-2-(4-iodophenyl)-2,3-dihydro-1,4-benzoxathiine.

Starting with the adduct 7e (2.00 g, 3.0 mmol), prepared in Example 7, and slightly modifying the procedure, the crude product was isolated after stirring at 0° C. to ambient temperature for 5 h and storage at 0° C. for 15 h. Purification by silica gel chromatography with 15% ethyl acetate/hexane as the eluant afforded the desired product as a white sticky gum. $^1$H NMR (500 MHz, CDCl$_3$) δ (ppm): 4.37 (d, J=2.3 Hz, 1H), 4.86 (m, 2H), 5.16 (s, 2H), 5.41 (d, J=2.0, 1H), 6.48–6.52 (m, 2H), 6.71–6.84 (m, 5H), 7.05 (t, 1H), 7.35–7.43 (m, 10H), 7.57 (d, 2H).

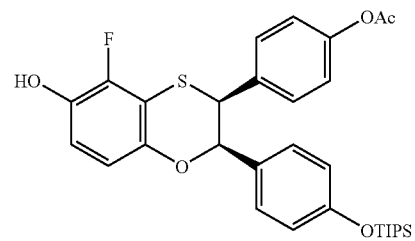

8e. 4-(5-fluoro-6-hydroxy-2-{4-[(triisopropylsilyl)oxy]phenyl}-2,3-dihydro-1,4-benzoxathiin-3-yl)phenyl acetate.

Utilizing the thioketone 7d, prepared in Example 7, the desired product was obtained. $^1$H NMR (500 MHz, CDCl$_3$) δ (ppm): 0.98 (d, 18H), 1.27 (m, 3H), 2.26 (s, 3H), 4.37 (d, J=2.1 Hz, 1H), 5.41 (d, J=2.1 Hz, 1H), 6.73–6.86 (m, 10H).

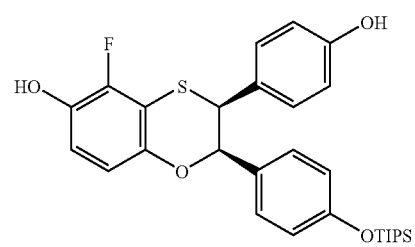

8f. 5-fluoro-3-(4-hydroxyphenyl)-2-{4-[(triisopropylsilyl)oxy]phenyl}-2,3-dihydro-1,4-benzoxathiin-6-ol.

To a solution of 8e (100.36 g, 187 mmol) in anhydrous TBF (1 liter), at 0° C. under nitrogen was added a 1 M solution of lithium triethylborohydride in TBF (561 mL) via a dropping funnel over 45 min. After stirring for 5 min., an additional 160 mL of super-hydride was added to the reaction in 20 mL increments until the starting material was consumed as monitored by TLC (15% ethyl acetate/hexane). After a total of 1 hour 15 min., the reaction was quenched with cold 2 N HCl. The mixture was extracted with ethyl acetate. The organic layer was collected, washed with brine, dried over sodium sulfate, and concentrated in vacuo. Purification by silica gel chromatography with 15% ethyl acetate/hexane as the eluant afforded the desired product as a yellow foam. $^1$H NMR (500 MHz, CDCl$_3$) δ (ppm): 1.10 (d, 18H), 1.27 (m, 3H), 4.34 (d, J=2.1 Hz, 1H), 5.41 (d, J=2.0 Hz, 1H), 6.59 (d, 2H), 6.75 (m, 6H), 6.85 (d, 2H).

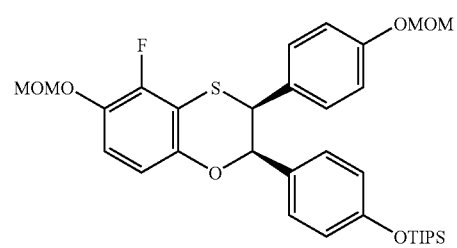

8g. 4-(5-fluoro-6-(methoxymethoxy)-3-[4-(methoxymethoxy)phenyl]-2,3-dihydro-1,4-benzoxathiin-2-yl}phenoxy)(triisopropyl)silane.

Utilizing the procedure outlined in Example 9, Step A, compound 8f was converted to the desired product, a tan solid. The crude material was azeotroped with toluene and used without further purification. $^1$H NMR (500 MHz, CDCl$_3$) δ (ppm): 1.10 (d, 18H), 1.27 (m, 3H), 3.44 (s, 3H), 3.58 (s, 3H), 4.34 (d, J=2.1 Hz, 1H), 5.11 (s, 2H), 5.19 (s, 2H), 5.43 (d, J=2.1 Hz, 1H), 6.74–6.79 (m, 7H), 6.86 (d, 2H), 6.94 (t, 1H).

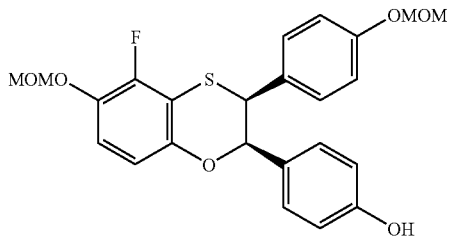

8h. 4-(5-fluoro-6-(methoxymethoxy)-3-[4-(methoxymethoxy)phenyl]-2,3-dihydro-1,4-benzoxathiin-2-yl}phenol.

Utilizing the procedure outlined in Example 9, Step B, compound 8g was converted to the desired product 8h. $^1$H NMR (500 MHz, CDCl$_3$) δ (ppm): 3.46 (s, 3H), 3.59 (s, 3H), 4.37 (d, J=2.3 Hz, 1H), 5.13 (s, 2H), 5.20 (s, 2H), 5.43 (d, J=1.8 Hz, 1H), 6.68–6.96 (m, 10H).

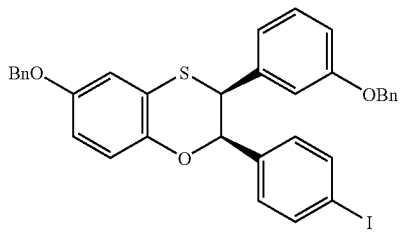

8i. 6-(benzyloxy)-3-[3-(benzyloxy)phenyl]-2-(4-iodophenyl)-2,3-dihydro-1,4-benzoxathiine.

Utilizing the requisite thioketone, prepared as described in Example 7, the desired product was obtained. $^1$H NMR (500 MHz, CDCl$_3$) δ (ppm): 7.58 (d, 2H), 7.5–7.3 (m),7.05 (t, 1H), 6.94 (d, 1H), 6.84 (d, 1H), 6.82–6.4 (m), 6.56 (t, 1H), 6.52 (d, 1H), 5.44 (d, 1H), 5.06 (s, 2H), 4.86 (q, 2H), 4.34 (d, 1H).

Example 9

Chiral Preparation of

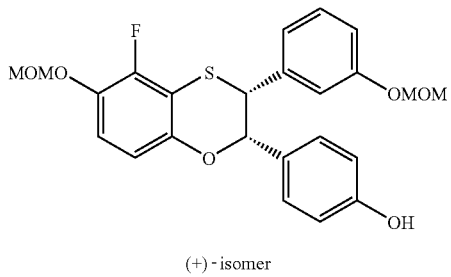

(+)-isomer

Preparation of (+)-4-{(2S,3R)-5-fluoro-6-(methoxymethoxy)-3-[3-(methoxymethoxy)phenyl]-2,3-dihydro-1,4-benzoxathiin-2-yl}phenol.

Step A:

To a solution of the product 8c, obtained from Example 8, (5.38 g, 10 mmol) in distilled THF (60 mL) at 0° C. under N$_2$ was added MOMCl (1.9 mL, 26 mmol) followed by portion-wise addition of 95% NaH (0.6164 g, 22 mmol). The reaction became dark green but with time became yellow/brown. After stirring for 1 h, the reaction appeared mostly complete by TLC (30% EtOAc/hexane). Additional MOMCl (1 mL) was added to drive the reaction to completion. After 15 min., the reaction was partitioned between EtOAc and ice/water. The organic layer was collected, washed with brine, dried over Na$_2$SO$_4$, filtered, and concentrated in vacuo. The crude residue was used without further purification. $^1$H 500 MHz NMR(CDCl$_3$) ppm(δ): 1.10 (d, 18H), 1.25 (m, 3H), 3.39 (s, 3H), 3.58 (s, 3H), 4.36 (d, J=2.1 Hz, 1H), 5.00 (m, 2H), 5.19 (s, 2H), 5.43 (d, J=1.9 Hz, 1H), 6.57–7.03 (m, 10H).

Step B:

To a solution of the isolate from Step A (10 mmol) in distilled THF (60 mL) was added AcOH (0.76 mL, 13 mmol) at 0° C. under N$_2$ followed by a 1 M solution of TBAF in THF (11 mL, 11 mmol). After 5 min., the reaction was complete and the reaction was partitioned between saturated NaHCO$_3$ and EtOAc. The organic layer was collected, washed with brine, dried over Na$_2$SO$_4$, filtered, and concentrated in vacuo. The crude material was purified by silica gel chromatography with 40% EtOAc/hexane as the eluant to afford the desired product as a light yellow solid. $^1$H 500 MHz NMR(CDCl$_3$) ppm(δ): 3.39 (s, 3H), 3.59 (s, 3H), 4.37 (d, J=2.3 Hz, 1H), 4.99 (s, 2H), 5.20 (s, 2H), 5.44 (d, J=2.1 Hz, 1H), 6.55–7.08 (m, 10H).

The racemic benzoxathiin was resolved via chiral chromatography on a Chiralcel® OD™ column (150 mm diameter), available from Daicel Chemical Industries, Ltd., using 20% iPrOH in heptane as the eluant (400 mL/min). The faster moving isomer was identified as the (+) enantiomer by a PDR-Chiral laser polarimeter.

Example 9A

Chiral Preparation of

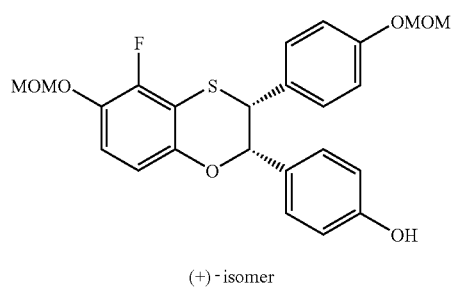

(+)-isomer

The racemic benzoxathiin 8h, from Example 8, was resolved via chiral chromatography on a Chiralpak AD 100×250 mm column, using isooctane:isopropanol 50:50 as the eluant (300 mL/min) and ~2.5 g racemate per injection with monitoring at 310 nM. The (+) enantiomer eluted at 8.8 min, and the (−) enantiomer eluted at 13.5 min.

The Analytical Conditions: Chiralcel AD 4.6×250 mm column, heptane:isopropanol 80:20, at 1 mL/min, at 220 nM. The (−) enantiomer eluted at 8.1 min, and the (+) enantiomer eluted at 9.7 min.

Example 10

Preparation of Dihydro-benzoxathiin Derivatives

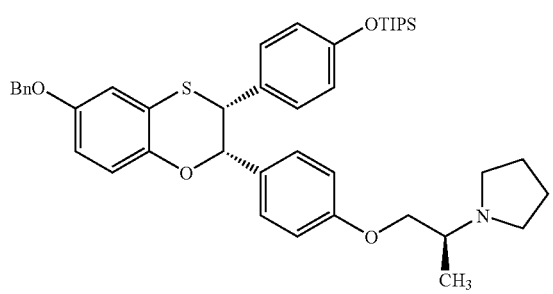

Preparation of 1-{(1S)-2-[4-((2S,3R)-6-(benzyloxy)-3-{4-[(triisopropylsilyl)oxy]phenyl}-2,3-dihydro-1,4-benzoxathiin-2-yl)phenoxy]-1-methylethyl}pyrrolidine (10a).

Step A:

To a stirred solution of a mixture of 242.6 mg (0.4 mmol) of (+)-4-((2S,3R)-6-(benzyloxy)-3-{3-[(triisopropylsilyl)oxy]phenyl}-2,3-dihydro-1,4-benzoxathiin-2-yl)phenol (8b), obtained from Example 8, triphenylphosphine (319 mg, 1.2 mmol), and (S)-2-pyrrolidino-1-propanol (157 mg, 1.2 mmol) in 4 mL of anhydrous TBF at ambient temperature was added dropwise 239 μL (1.2 mmol) of diisopropyl azodicarboxylate (DIAD). The resulting solution was stirred further for 18.5 hours. The mixture was partitioned between ethyl acetate/2N HCl. The organic phase was separated and washed with a mixture of brine and saturated sodium bicarbonate, and again with brine; dried over anhydrous sodium sulfate; filtered, and evaporated. The residue was purified by plate layer silica gel chromatography (PLC) using ethyl acetate as the eluant to give the normal product (NMR given in table below), and the rearranged product. $^1$H NMR (500 MHz, CDCl$_3$) δ (ppm): 7.5–7.34 (m, 5H), 6.9–6.7 (m, 10H), 6.26 (d, 1H), 5.46 (d, 1H), 5.01 (s, 2H), 4.26 (d, 1H), 4.05 (t, 2H), 2.87 (t, 2H), 2.6 (m, 4H), 1.8 (m, 4H), 1.22 (m, 3H), 0.97 (d, 18H).

Utilizing the foregoing procedure and the appropriate chiral pyrrolidine-ethanol derivative the following compounds were prepared:

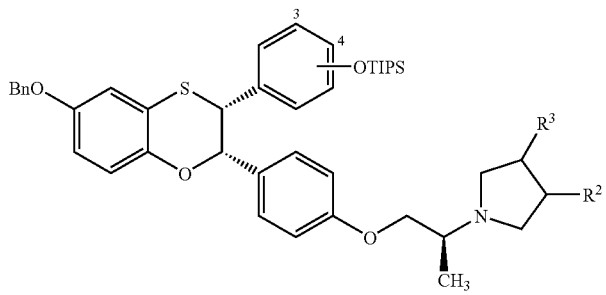

| R$^2$ | R$^3$ | OTIPS position | Spectroscopic Data ($^1$H 500 MHz NMR, δ, ppm, CDCl$_3$/Mass Spec.) |
|---|---|---|---|
| H | H | 4 | 1.08 (d, 21H), 1.23 (m, 3H), 1.8 (m, 4H), 2.69 (m, 5H), 3.8 (m, 1H), 4.05 (m, 1H), 4.3 (d, J = 2 Hz, 1H), 5.04 (s, 2H), 5.42 (d, J = 2 Hz, 1H), 6.64–6.92 (m, 11H), 7.35–7.47 (m, 5H) |
| H | H | 3 | 0.99 (d, 21H), 1.03 (m, 3H), 1.8 (m, 4H), 2.7 (m, 5H), 3.86 (m, 1H), 4.06 (m, 1H), 4.3 (d, J = 2 Hz, 1H), 5.05 (s, 2H), 5.49 (d, J = 2 Hz, 1H), 6.34 (d, J = 7.6 Hz, 1H), 6.7–6.98 (m, 10H), 7.36–7.48 (m, 5H) |
| β-CH$_3$ | H | 4 | 1.09 (d, 21H), 1.24 (m, 4H), 2.0–3.1 (m's, 7H), 3.8 (m, 1H), 4.05 (m, 1H), 4.3 (d, J = 2 Hz, 1H), 5.05 (s, 2H), 5.42 (d, J = 2 Hz, 1H), 6.66–6.93 (m, 11H), 7.36–7.48 (m, 5H) |
| β-CH$_3$ | α-CH$_3$ | 4 | 1.01 (d, 6H), 1.07 (d, 18H), 1.20 (d, 3H), 1.20 (m, 3H), 1.70 (m, 2H), 2.41 (m, 2H), 2.76–2.95 (m, 3H), 3.80 (m, 1H), 4.02 (m, 1H), 4.29 (d, J = 2.2 Hz, 1H), 5.01 (s, 2H), 5.40 (d, J = 2.1 Hz, 1H), 6.63–6.90 (m, 11H), 7.33–7.50 (m, 5H) |
| α-CH$_3$ | β-CH$_3$ | 4 | 1.02 (d, 6H), 1.07 (d, 18H), 1.20 (d, 3H), 1.22 (m, 3H), 1.72 (m, 2H), 2.42 (m, 2H), 2.75–2.97 (m, 3H), 3.75 (m, 1H), 4.02 (m, 1H), 4.29 (d, J = 2.0 Hz, 1H), 5.03 (s, 2H), 5.40 (d, J = 1.8 Hz, 1H), 6.64–6.91 (m, 11H), 7.34–7.45 (m, 5H) |
| β-CH$_3$ | β-CH$_3$ | 4 | 0.94 (2 d's, 6H), 1.07 (d, 18H), 1.23 (d, 3H), 1.23 (m, 3H), 2.10 (m, 2H), 2.29 (m, 2H), 2.72 (m, 1H), 3.20 (m, 2H), 3.79 (m, 1H), 4.02 (m, 1H), 4.29 (d, J = 2.2 Hz, 1H), 5.03 (s, 2H), 5.41 (d, J = 2.0 Hz, 1H), 6.64–6.91 (m, 11H), 7.34–7.45 (m, 5H) |

-continued

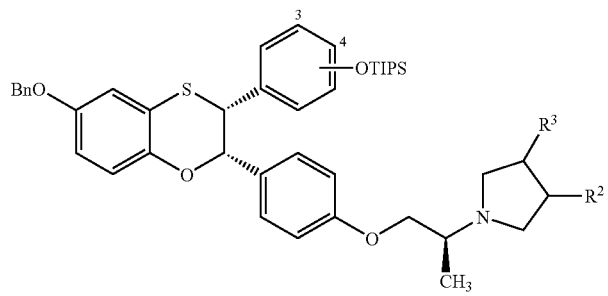

| $R^2$ | $R^3$ | OTIPS position | Spectroscopic Data ($^1$H 500 MHz NMR, δ, ppm, CDCl$_3$/Mass Spec.) |
|---|---|---|---|
| β-CH$_3$ | α-CH$_3$ | 3 | 0.99–1.04 (m, 27H), 1.6–3.0 (m, 7H), 3.8 (m, 1H), 4.07 (m, 1H), 4.29 (d, 1H), 5.04 (s, 2H), 5.48 (d, 1H), 6.32 (d, 1 = 7.6 Hz, 1H), 6.7–6.96 (m, 10H), 7.35–7.48 (m, 5H) |
| β-CH$_3$ | H | 3 | 0.98 (d, 18H), 1.01 (d, 3H), 1.01 (m, 3H), 1.21 (d, 3H), 1.36 (m, 1H), 2.02 (m, 1H), 2.15 (m, 1H), 2.23 (m, 1H), 2.60 (m, 1H), 2.75 (m, 1H), 2.91 (m, 1H), 3.03 (m, 1H), 3.81 (m, 1H), 4.02 (m, 2H), 4.28 (d, J = 2.2 Hz, 1H), 5.03 (s, 2H), 5.43 (d, J = 2.0 Hz, 1H), 6.31 (d, 1H), 6.66–6.97 (m, 11H), 7.34–7.45 m, 5H) |
| α-CH$_3$ | H | 3 | 1.09 (d, 21H), 1.25 (m, 3H), 2.0–3.1 (m's, 7H), 3.8 (m, 1H), 4.05 (m, 1H), 4.31 (d, J = 2 Hz, 1H), 5.05 (s, 2H), 5.43 (d, J = 2 Hz, 1H), 6.65–6.93 (m, 11H), 7.36–7.48 (m, 5H) |

30

Step A:

Utilizing the foregoing procedure with the chiral material prepared in Example 9 and the appropriate chiral pyrrolidine-ethanol derivative the following compounds were prepared:

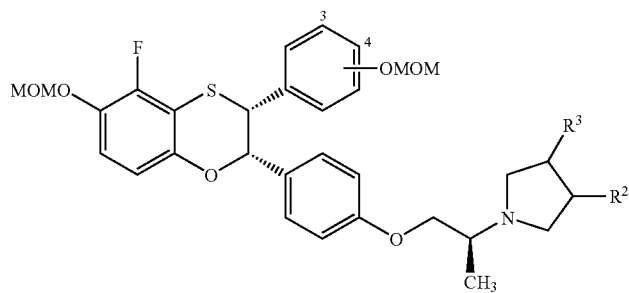

| $R^2$ | $R^3$ | OMOM position | Spectroscopic Data ($^1$H 500/600 MHz NMR, δ, ppm, CDCl$_3$/Mass Spec.) |
|---|---|---|---|
| β-CH$_3$ | H | 4 | 1.05 (d, 3H), 1.27 (d, 3H), 1.40 (m, 1H), 2.03–2.31 (m, 3H), 2.65 (m, 1H), 2.80 (m, 1H), 2.94 (m, 1H), 3.09 (m, 1H), 3.45 (s, 3H), 3.57 (s, 3H), 3.87 (m, 1H), 4.08 (m, 1H), 4.36 (d, J = 1.9 Hz, 1H), 5.12 (m, 2H), 5.17 (s, 2H), 5.42 (d, J = 1.6 Hz, 1H), 6.73–6.94 (m, 10H). |
| α-CH$_3$ | β-CH$_3$ | 3 | 1.03 (d, 6H), 1.74 (m, 2H), 2.39 (m, 2H), 2.83–2.92 (m, 4H), 3.37 (s, 3H), 3.57 (s, 3H), 4.03 (m, 2H), 4.37 (d, J = 2.2 Hz, 1H), 4.97 (s, 2H), 5.18 (s, 2H), 5.43 (d, J = 2.1 Hz, 1H), 6.55–7.07 (m, 10H) |
| H | H | 3 | 1.22 (d, 3H), 1.81 (m, 4H), 2.68 (m, 5H), 3.39 (s, 3H), 3.59 (s, 3H), 3.83 (m, 1H), 4.02 (m, 1H), 4.37 (d, J = 1.9 Hz, 1H), 4.96 (s, 2H), 5.17 (s, 2H), 5.43 (d, J = 1.8 Hz, 1H), 6.54–7.08 (m, 10H) |

-continued

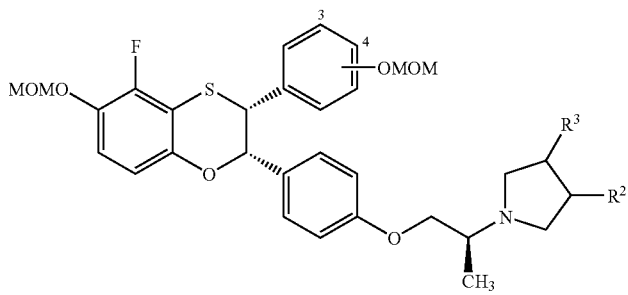

| R² | R³ | OMOM position | Spectroscopic Data (¹H 500/600 MHz NMR, δ, ppm, CDCl₃/Mass Spec.) |
|---|---|---|---|
| β-CH₃ | β-CH₃ | 3 | 0.90 (2 d's, 6H), 1.21 (d, 3H), 2.12 (m, 2H), 2.29 (m, 2H), 2.73 (m, 1H), 3.20 (m, 2H), 3.39 (s, 3H), 3.59 (s, 3H), 3.80 (m, 1H), 4.02 (m, 1H), 4.39 (d, J = 2.3 Hz, 1H), 4.98 (s, 2H), 5.19 (s, 2H), 5.42 (d, J = 2.3 Hz, 1H), 6.54–7.08 (m, 10H) |
| β-CH₃ | H | 3 | 1.01 (d, 3H), 1.21 (d, 3H), 1.36 (m, 1H), 2.02 (m, 1H), 2.10 (t, 1H), 2.23 (m, 1H), 2.58 (m, 1H), 2.70 (m, 1H), 2.87 (m, 1H), 3.00 (t, 1H), 3.39 (s, 3H), 3.59 (s, 3H), 3.81 (m, 1H), 4.02 (m, 1H), 4.38 (d, J = 2.3 Hz, 1H), 4.96 (s, 2H), 5.17 (s, 2H), 5.43 (d, J = 2.3 Hz, 1H), 6.54–7.08 (m, 10H) |

Example 10A

Preparation of

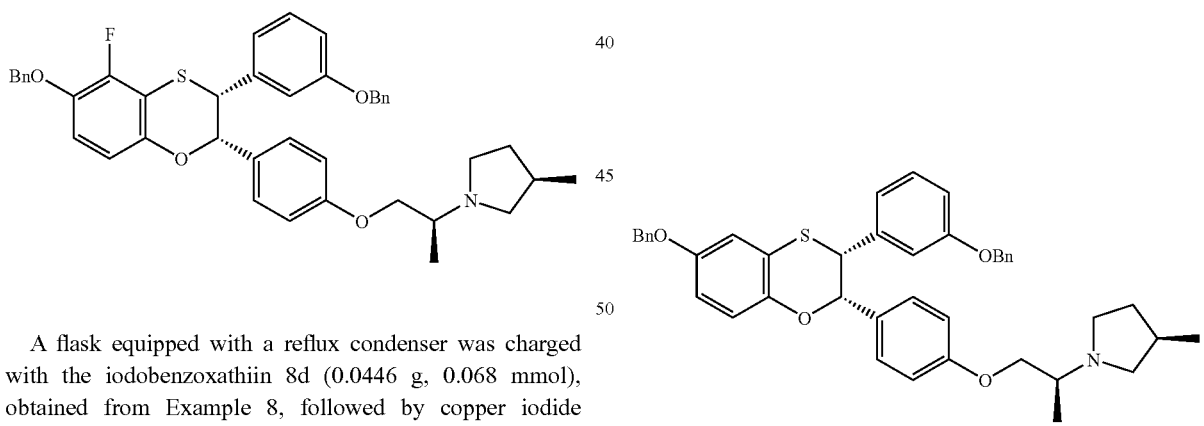

A flask equipped with a reflux condenser was charged with the iodobenzoxathiin 8d (0.0446 g, 0.068 mmol), obtained from Example 8, followed by copper iodide (0.0017 g, 0.0068 mmol), 2,2'-dipydidyl (0.0016 g, 0.0082 mmol), and potassium carbonate (0.0284 g, 0.20 mmol). Xylene (0.5 mL) was then added to the flask followed by (2S)-2-[(3R)-3-methylpyrrolidin-1-yl]propan-1-ol (0.048 g, 0.34 mmol). The reaction was degassed and heated to 140° C. under nitrogen for 21 h. The reaction was diluted with toluene and filtered through celite. The filtrate was partitioned between ethyl acetate and ice/2 N HCl. The organic layer was collected, washed with saturated sodium bicarbonate and brine, dried over sodium sulfate, and concentrated in vacuo to give a brown oil. The crude material was purified by silica gel chromatography with 10% methanol/methylene chloride as the eluant to give the desired product as an orange foam.

Example 10B

Preparation of

Similarly, following the procedure described in Example 10A and utilizing the iodobenzoxathiin derivative 8i, from Example 8, the above compound was obtained. ¹H NMR (500 MHz, CDCl₃) δ (ppm): 7.5–7.3 (m), 7.04 (t, 1H), 6.94 (dd, 2H), 6.83 (d, 1H), 6.79 (d, 2H), 6.74 (dd, 1H), 6.62 (brt, 1H), 6.56 (d, 1H), 5.48 (d, 1H), 5.06 (s, 2H), 4.86 (q, 2H), 4.34 (d, 1H), 4.04 (dd, 1H), 3.82 (dd, 1H), 3.0 (t, 1H), 2.9 (m, 1H), 2.7 (m, 1H), 2.55 (m, 1H), 2.3 (m, 1H), 2.1 (t, 1H), 2.02 (m, 1H), 1.35 (m, 1H), 1.22 (d, 3H), 1.05 (d, 3H).

Example 11

Preparation of Dihydro-benzoxathiins

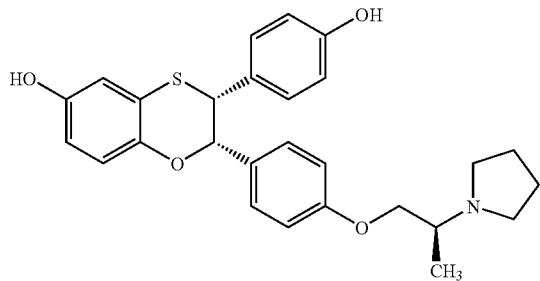

Preparation of (2S,3R)-3-(4-hydroxyphenyl)-2-(4-{[(2S)-2-pyrrolidin-1-ylpropyl]oxy}phenyl)-2,3-dihydro-1,4-benzoxathiin-6-ol (11a).

Step A:

A stirred mixture of 102 mg (0.14 mmol) of compound 10a, generated in Example 10, Step A, 30.6 mg (0.29 mmol) of palladium black and 181.2 mg (0.29 mmol) ammonium formate in 3 mL of EtOH/EtOAc/H$_2$O (7:2:1) was heated at 80° C. for 2 h. The reaction mixture was filtered through a pad of Celite® to remove the catalyst, washed thoroughly with EtOH/EtOAc/H$_2$O (7:2:1), and the filtrate was partitioned between water and EtOAc. The organic phase was separated, dried over Na$_2$SO$_4$, filtered, evaporated, and dried in vacuo to give the crude product which was used without purification.

Step B:

To a stirred solution of a mixture of the debenzylated product (87.2 mg, 0.14 mmol), generated in Step B, and 49.2 μL (0.84 mmol) of HOAc in 2 mL of TEF was added 281 μL (0.28 mmol) a 1M solution of tetrabutylammonium fluoride in THF at room temperature. The resulting solution was allowed to stir for three hours at room temperature. The mixture was partitioned between EtOAc, saturated aqueous NaHCO$_3$ and brine and the organic layer was separated, washed with brine, dried over Na$_2$SO$_4$, filtered, and evaporated. Purification by plate layer silica gel chromatography using EtOAC-MeOH (9:1) as the eluant afforded the desired product (NMR given in the table below).

Step C:

Using the MOM-protected-fluorine containing adducts, from Step A' in Example 10, a MeOH solution was treated with 2 N HCl and heated to 80° C. under N$_2$ for 45 min. The reaction was partitioned between EtOAc and ice/saturated NaHCO$_3$. The organic layer was collected, washed with brine, dried over Na$_2$SO$_4$, filtered, and evaporated. Purification by plate layer silica gel chromatography using either methylene chloride/methanol (9:1) or methylene chloride/ethyl acetate (9:1) as the eluants gave the following compounds listed in the table.

Utilizing the foregoing procedures the following compounds were prepared:

| R$^1$ | R$^2$ | R$^3$ | R$^4$ | R$^8$ | R$^7$ | position | Spectroscopic Data ($^1$H 500 MHz NMR, δ, ppm, d$_6$-acetone/Mass Spec./[α]) |
|---|---|---|---|---|---|---|---|
| H | H | H | α-CH$_3$ | β-CH$_3$ | H | 3 | 1.05 (2d, 6H), 1.33 (m, 1H), 1.65–1.70 (m, 2H), 1.86 (m, 1H), 2.64 (m, 1H), 2.82–2.84 (m, 2H), 3.26 (m, 1H), 3.84 (m, 1H), 4.02 (m, 1H), 4.54 (d, J = 2.3Hz, 1H), 5.46 (d, J = 2.3 Hz, 1H), 6.42 (d, 1H), 6.59–6.66 (m, 4H), 6.81 (d, 2H), 6.83 (d, 1H), 6.92 (t, 1H), 7.08 (d, 2H); MS m/z 478.1 (M$^+$ + 1). |
| H | H | H | α-CH$_3$ | α-CH$_3$ | H | 3 | 1.03 (d, 3H), 1.19 (d, 3H), 1.33 (m, 1H), 1.63–1.72 (m, 2H), 1.84 (m, 1H), 2.64 (m, 1H), 2.96 (m, 1H), 3.06 (m, 1H), 3.26 (m, 1H), 3.84 (m, 1H), 4.10 (m, 1H), 4.54 (d, J = 2.3 Hz, 1H), 5.46 (d, J = 2.2 Hz, 1H), 6.42 (d, 1H), 6.59–6.66 (m, 4H), 6.81 (d, 2H), 6.83 (d, 1H), 6.92 (t, 1H), 7.08 (d, 2H); MS m/z 478.1 (M$^+$ + 1). |
| H | H | H | β-CH$_3$ | α-CH$_3$ | H | 3 | 1.05 (2d, 6H), 1.33 (m, 1H), 1.65–1.70 (m, 2H), 1.86 (m, 1H), |

-continued

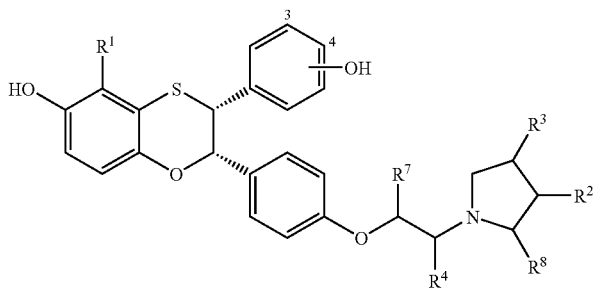

| R¹ | R² | R³ | R⁴ | R⁸ | R⁷ | position | Spectroscopic Data ($^1$H 500 MHz NMR, δ, ppm, $d_6$-acetone/Mass Spec./[α]) |
|---|---|---|---|---|---|---|---|
|  |  |  |  |  |  |  | 2.64 (m, 1H), 2.82–2.84 (m, 2H), 3.26 (m, 1H), 3.84 (m, 1H), 4.02 (m, 1H), 4.54 (d, J = 2.3 Hz, 1H), 5.46 (d, J = 2.3 Hz, 1H), 6.42 (d, 1H), 6.59–6.66 (m, 4H), 6.81 (d, 2H), 6.83 (d, 1H), 6.92 (t, 1H), 7.08 (d, 2H); MS m/z 478.1 (M⁺ + 1). |
| H | H | H | β-CH₃ | β-CH₃ | H | 3 | 1.03 (d, 3H), 1.19 (d, 3H), 1.33 (m, 1H), 1.63–1.72 (m, 2H), 1.84 (m, 1H), 2.64 (m, 1H), 2.96 (m, 1H), 3.06 (m, 1H), 3.26 (m, 1H), 3.84 (m, 1H), 4.10 (m, 1H), 4.54 (d, J = 2.3 Hz, 1H), 5.46 (d, J = 2.2 Hz, 1H), 6.42 (d, 1H), 6.59–6.66 (m, 4H), 6.81 (d, 2H), 6.83 (d, 1H), 6.92 (t, 1H), 7.08 (d, 2H); MS m/z 478.1 (M⁺ + 1). |
| F | β-CH₃ | H | H | H | α-CH₃ | 3 | 0.98 (d, 3H), 1.21 (d, 3H), 1.22 (m, 1H), 1.93 (m, 1H), 2.15 (m, 2H), 2.53–2.80 (m, 5H), 4.52 (m, 1H), 4.61 (d, J = 2.3 Hz, 1H), 5.46 (d, J = 2.0 Hz, 1H), 6.41 (d, 1H), 6.59–6.81 (m, 6H), 6.91 (t, 1H), 7.07 (d, 2H); MS m/z 496.1 (M⁺ + 1) |
| F | α-CH₃ | H | α-CH₃ | H | H | 3 | 0.98 (d, 3H), 1.14 (d, 3H), 1.25 (m, 1H), 1.93 (m, 1H), 2.16 (m, 2H), 2.64–2.90 (m, 4H), 3.77 (m, 1H), 4.05 (m, 1H), 4.60 (d, J = 2.3 Hz, 1H), 5.45 (d, J = 2.2 Hz, 1H), 6.41 (d, 1H), 6.59–6.81 (m, 6H), 6.91 (t, 1H), 7.07 (d, 2H); MS m/z 496.4 (M⁺ + 1) |
| F | β-CH₃ | H | β-CH₃ | H | H | 4 | 0.99 (d, 3H), 1.17 (d, 3H), 1.27 (m, 1H), 1.97 (m, 1H), 2.18 (m, 2H), 2.63–2.90 (m, 4H), 3.79 (m, 1H), 4.07 (m, 1H), 4.60 (d, J = 2.0 Hz, 1H), 5.46 (d, J = 2.1 Hz, 1H), 6.60 (d, 2H), 6.71–6.83 (m, 8H), 7.05 (d, 2H), MS m/z 496.1 (M⁺ + 1) |
| H | H | H | β-CH₃ | H | H | 4 | 1.18 (d, J = 6.6 Hz, 3H), 1.8 (m, 4H), 2.62 (m, 4H), 2.7 (m, 1H), 3.8 (m, 1H), 4.08 (m, 1H), 4.53 (d, J = 2 Hz, 1H), 5.44 (d, J = 2 Hz, 1H), 6.58 (m, 2H), 6.59 (d, J = 8.5 Hz, 2H), 6.6 (d, J = 3 Hz, 1H), 6.8 (d, J = 8.7 Hz, 2H), 6.83 (d, J = 8.5 Hz, 2H), 7.05 (d, J = 8.7 Hz, 2H) |
| H | H | H | β-CH₃ | H | H | 3 | 1.18 (d, J = 6.4 Hz, 3H), 1.8 (m, 4H), 2.63 (m, 4H), 2.7 (m, 1H), 3.79 (m, 1H), 4.07 (m, 1H), 4.54 (d, J = 2.0 Hz, 1H), 5.45 (d, J = 2 Hz, 1H), 6.42 (d, J = 7.3 Hz, 1H), 6.59 (m, 1H), 6.64 (m, 4H), 6.8 (d, J = 8.7 Hz, 2H), 6.84 (d, J = 8.7 Hz, 1H), 6.92 (t, J = 7.6 Hz, 1H), 7.09 d, J = 8.7 Hz, 2H) |

-continued

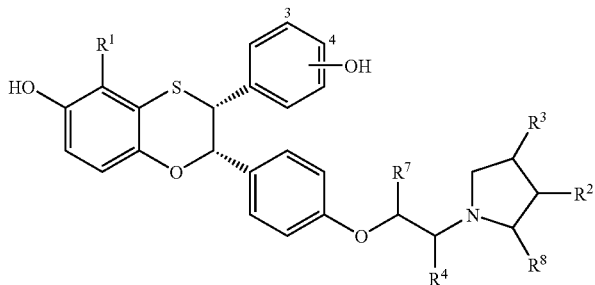

| R¹ | R² | R³ | R⁴ | R⁸ | R⁷ | position | Spectroscopic Data (¹H 500 MHz NMR, δ, ppm, d₆-acetone/Mass Spec./[α]) |
|---|---|---|---|---|---|---|---|
| F | α-CH₃ | β-CH₃ | β-CH₃ | H | H | 3 | 0.99 (d, 6H), 1.66 (m, 2H), 2.29 (m, 2H), 2.80 (m, 4H), 4.01 (m, 2H), 4.60 (d, J = 2.3 Hz, 1H), 5.45 (d, J = 2.3 Hz, 1H), 6.40 (d, 1H), 6.58–6.80 (m, 6H), 6.91 (t, 1H), 7.06 (d, 2H); MS m/z 496.2 (M⁺) |
| F | H | H | β-CH₃ | H | H | 3 | 1.19 (d, 3H), 1.71 (m, 4H), 2.65–2.90 (m, 5H), 3.80 (m, 1H), 4.08 (m, 1H), 4.60 (d, J = 2.2 Hz, 1H), 5.45 (d, J = 2.2 Hz, 1H), 6.41 (d, 1H), 6.59–6.81 (m, 6H), 6.92 (t, 1H), 7.07 (d, 2H); MS m/z 482.2 (M⁺) |
| H | β-CH₃ | H | β-CH₃ | H | H | 4 | 0.99 (d, J = 6.6 Hz, 3H), 1.15 (d, J = 6.4 Hz, 3H), 1.27 (m, 1H), 1.9–2.9 (m's, 7H), 3.78 (m, 1H), 4.05 (m, 1H), 4.52 (d, J = 1 Hz, 1H), 5.43 (d, J = 2.1 Hz, 1H), 6.58 (m, 2H), 6.59 (d, J = 8.5 Hz, 2H), 6.6 (d, J = 3 Hz, 1H), 6.79 (d, J = 8.6 Hz, 2H), 6.82 (d, J = 7.4 Hz, 2H), 7.03 (d, J = 8.7 Hz, 2H) |
| H | β-CH₃ | α-CH₃ | β-CH₃ | H | H | 4 | 0.98 (d, 6H), 1.13 (d, 3H), 1.62 (m, 2H), 2.33 (m, 2H), 2.73 (m, 1H), 2.91 (m, 2H), 3.77 (m, 1H), 4.04 (m, 1H), 4.50 (d, J = 2.2 Hz, 1H), 5.42 (d, J = 2.1 Hz, 1H), 6.57–7.03 (m, 1H); MS m/z 492.3 (M⁺) |
| H | α-CH₃ | β-CH₃ | β-CH₃ | H | H | 4 | 0.98 (d, 3H), 1.07 (d, 3H), 1.15 (d, 3H), 1.62 (m, 2H), 2.35 (m, 2H), 2.71 (m, 1H), 2.89 (m, 2H), 3.71 (m, 1H), 4.03 (m, 1H), 4.51 (d, J = 2.2 Hz, 1H), 5.42 (d, J = 2.0 Hz, 1H), 6.56–6.82 (m, 9H), 7.02 (d, 2H); MS m/z 492.3 (M⁺) |
| H | β-CH₃ | β-CH₃ | β-CH₃ | H | H | 4 | 0.89 (2 d's, 6H), 1.14 (d, 3H), 2.19 (m, 2H7), 2.71–2.90 (m, 3H), 3.05 (m, 2H), 3.74 (m, 1H), 4.03 (m, 1H), 4.51 (d, J = 2.2 Hz, 1H), 5.42 (d, J = 2.2 Hz, 1H), 6.56–6.82 (m, 9H), 7.02 (d, 2H); MS m/z 492.3 (M⁺) |
| F | β-CH₃ | H | β-CH₃ | H | H | 3 | 0.99 (d, 3H), 1.15 (d, 3H), 1.26 (m, 1H), 1.93 (m, 1H), 2.16 (m, 2H), 2.62–2.89 (m, 4H), 3.77 (m, 1H), 4.04 (m, 1H), 4.60 (d, J = 2.3 Hz, 1H), 5.45 (d, J = 2.1 Hz, 1H), 6.40 (d, 1H), 6.59–6.80 (m, 6H), 6.91 (t, 1H), 7.07 (d, 2H); MS m/z 496.2 (M⁺); [α]_D = +219° (c = 1.03, MeOH) |
| H | β-CH₃ | α-CH₃ | β-CH₃ | H | H | 3 | 0.99 (d, 6H), 1.18 (d, 3H), 1.6–2.9 (m, 7H), 3.77 (m, 1H), 4.04 (m, 1H), 4.53 (d, 1H), 5.45 (d, 1H), 6.4–7.07 (m, 11H) |
| F | β-CH₃ | β-CH₃ | β-CH₃ | H | H | 3 | 0.89 (2 d's, 6H), 1.13 (d, 3H), 2.18 (m, 2H), 2.72–2.91 (m, 3H), 3.01 (m, 2H), 3.74 (m, 2H), 4.05 (m, 2H), 4.60 (d, J = 2.3 Hz, 1H), |

-continued

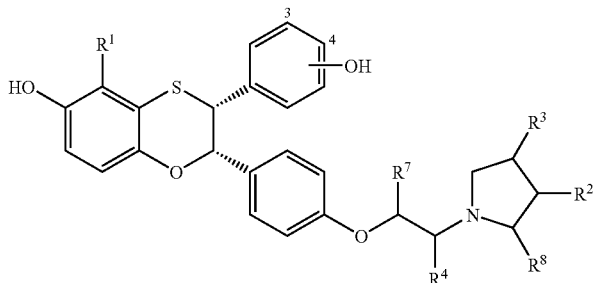

| $R^1$ | $R^2$ | $R^3$ | $R^4$ | $R^8$ | $R^7$ | position | Spectroscopic Data ($^1$H 500 MHz NMR, δ, ppm, $d_6$-acetone/Mass Spec./[α]) |
|---|---|---|---|---|---|---|---|
| H | β-CH$_3$ | H | β-CH$_3$ | H | H | 3 | 5.45 (d, J = 2.2 Hz, 1H), 6.40 (d, 1H), 6.59–6.80 (m, 6H), 6.91 (t, 1H), 7.07 (d, 2H); MS m/z 510.0 (M$^+$) 0.98 (d, 3H), 1.14 (d, 3H), 1.26 (m, 1H), 1.92 (m, 1H), 2.16 (m, 2H), 2.62 (m, 1H), 2.70 (m, 2H), 2.88 (m, 1H), 3.76 (m, 1H), 4.04 (m, 1H), 4.52 (d, J = 2.3 Hz, 1H), 5.43 (d, J = 2.2 Hz, 1H), 6.40 (d, 1H), 6.57–6.82 (m, 7H), 6.90 (t, 1H), 7.06 (d, 2H); MS m/z 478.1 (M$^+$) |
| H | α-CH$_3$ | H | β-CH$_3$ | H | H | 4 | 1.0 (d, J = 6.2 Hz, 3H), 1.17 (d, J = 6.4 Hz, 3H), 1.27–2.9 (m, 8H), 3.76 (m, 1H), 4.06 (m, 1H), 4.53 (d, J = 2.1 Hz, 1H), 5.44 (d, J = 2 Hz, 1H), 6.59 (m, 4H), 6.6 (d, J = 3 Hz, 1H), 6.8 (d, J = 8.7 Hz, 2H), 6.83 (d, J = 8.4 Hz, 2H), 7.04 (d, J = 8.7 Hz, 2H) |

Example 11A

Preparation of

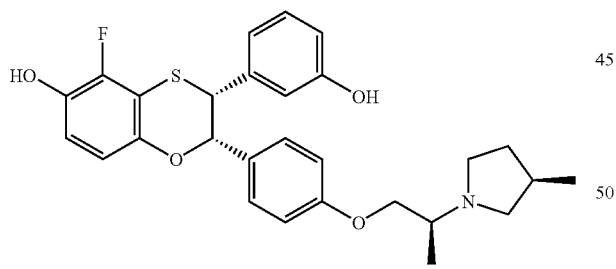

To a mixture of the benzoxathiins obtained from Example 10A (0.0276 g, 0.041 mmol) in acetonitrile (0.2 mL) was added iodotrimethylsilane (0.026 mL, 0.18 mmol) under nitrogen. The reaction was wrapped with aluminum foil and stirred at ambient temperature for 19.5 h. Thiourea (0.0141 g, 0.017 mmol) was added to the reaction and the resulting mixture was stirred for 1 h. The reaction was quenched with methanol and partitioned between ethyl acetate and ice/saturated sodium bicarbonate/5% sodium thiosulfate. The organic layer was collected, washed with brine, dried over sodium sulfate and concentrated in vacuo. The crude material was purified by silica gel chromatgoraphy to give the desired product.

$^1$H 500 MHz NMR($d_6$-acetone) ppm(δ): 0.99 (d, 3H), 1.17 (d, 3H), 1.27 (m, 1H), 1.97 (m, 1H), 2.18 (m, 2H), 2.63–2.90 (m, 4H), 3.79 (m, 1H), 4.07 (m, 1H), 4.60 (d, J=2.0 Hz, 1H), 5.46 (d, J=2.1 Hz, 1H), 6.60 (d, 2H), 6.71–6.83 (m, 8H), 7.05 (d, 2H).

Example 12

Preparation of 2(S)-pyrrolidinyl-propan-1-ol

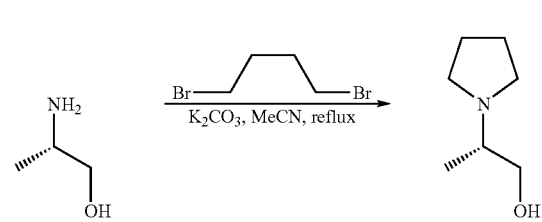

Potassium carbonate (41.4 g, 0.30 moles) was added to a solution of (S)-(+)-2-amino-1-propanol (11.27 g, 0.15 moles, Aldrich) in anhydrous acetonitrile (1.5 L) then 1,4-dibromobutane (17.9 mL, 0.15 moles, Aldrich) was added. The resulting mixture was refluxed for 24 hours then cooled to room temperature and filtered. The filtrate was concentrated under vacuum to a straw-colored solid which was dissolved in dichloromethane (150 mL) and again concentrated under vacuum to afford a straw-colored solid. This crude material, believed to be a mixture of the hydrobromide salt and the free base of the product, was again dissolved in dichloromethane (200 mL). Solid potassium carbonate and the mixture was stirred vigorously for 3 hours then filtered and concentrated under vacuum to afford a straw-colored solid. This solid, believed to still be partially the hydrobromide salt, was partitioned between dichloromethane (150 mL) and saturated aqueous potassium carbonate (50 mL). The layers (upper layer organic, lower layer aqueous) were separated and the aqueous layer was extracted with dichloromethane (2×100 mL). The combined organic layers were dried over magnesium sulfate, filtered and evaporated to an amber oil. This crude product was purified by short-path vacuum distillation to afford the title compound as a colorless liquid (bp 53–54.5° C. at 1.5 mm Hg). NMR: (CDCl$_3$, 600 MHz) δ 3.59 & 3.36 (2H, 2 dd, J=4, 10 Hz, H$_1$), 2.64–2.72 (1H, m, H$_2$), 2.54–2.62 (4H, m, H$_{2'}$ & H$_{5'}$), 1.72–1.80 (4H, m, H$_{3'}$ & H$_{4'}$),1.04 (3H, d, J=7 Hz, H$_3$); MS (electrospray): m/e 130 (M+H), 112 (M–OH). [α]$_D$+0.9°

Example 13

Preparation of 2(S)-(3-(R)-methylpyrrolidinyl)-propan-1-ol

Procedure A

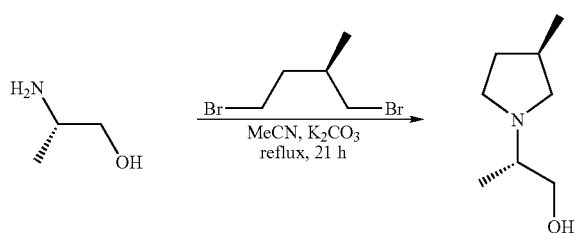

A solution of 2-(R)-methyl-1,4-dibromobutane (9.50 g, 0.041 moles) in anhydrous acetonitrile (25 mL) was added to a mixture of of (S)-(+)-2-amino-1-propanol (3.10 g, 0.041 moles, Aldrich) and potassium carbonate (11.42 g, 0.082 moles) in anhydrous acetonitrile (325 mL). The resulting mixture was refluxed for 21 hours then cooled to room temperature and concentrated under vacuum to an oily solid residue. Ether (200 mL) and saturated aqueous potassium carbonate (25 mL) were added followed by just enough water to dissolve all solid. The layers (upper layer organic, lower layer aqueous) were separated and the aqueous layer was saturated with sodium chloride and extracted with dichloromethane (2×100 mL). The combined organic layers were dried over magnesium sulfate and potassium carbonate, filtered and evaporated to a yellow liquid. This crude product was purified by short-path vacuum distillation to afford the title compound as a colorless liquid (4.0 g, bp 54–57° C. at ~3 mm Hg). A portion (2.31 g) of this material was further purified by column chromatography on silica gel eluted with 10:7:2:1 ethyl acetate:hexane:methanol:triethylamine to afford the title compound as a colorless liquid. NMR: (CDCl$_3$, 600 MHz) δ3.57 & 3.33 (2H, 2 dd, J=5, 10 Hz, H$_1$), 3.06 (1H, br s, OH), 2.85 (1H, dd, J=8, 9 Hz, H$_{2'a}$), 2.68–2.73 (1H, m, H$_2$), 2.66–2.70 & 2.58–2.62 (4H, 2m, H$_{5'}$), 2.18–2.26 (1H, m, H$_{3'}$), 2.15 (1H, dd, J=7, 9 Hz, H$_{2'b}$), 1.94–2.02 & 1.30–1.38 (4H, 2m, & H$_{4'}$), 1.02 (3H, d, J=7 Hz, H$_{3'Me}$), 1.01 (3H, d, J=7 Hz, H$_3$); MS (electrospray): m/e 144 (M+H), 126 (M–OH). [α]$_D$–0.5°

Procedure B

Step 1: (3R)-1-[(1S)-2-hydroxy-1-methylethyl]-3-methylpyrrolidine-2,5-dione.

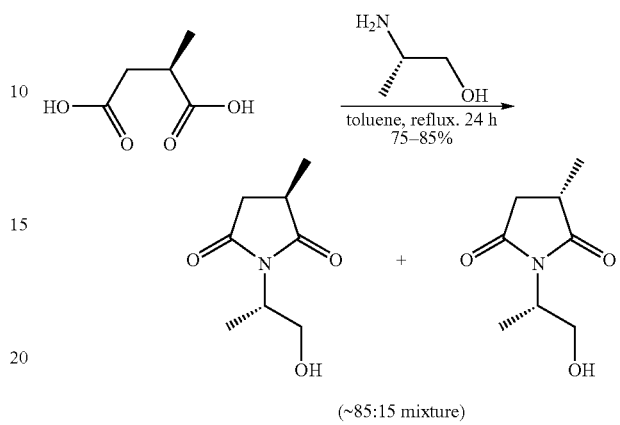

(~85:15 mixture)

(S)-(+)-2-Amino-1-propanol (7.80 mL, 100 mmol) was added to a hot (~100° C.) solution of 2-(R)-methylsuccinic acid (13.2 g, 100 mmol) in toluene (1.0 L) (note: the acid is not soluble at room temperature but dissolved on heating). The resulting cloudy mixture was refluxed under a Dean-Stark trap for 24 hours (2 L heating mantle; variac setting 45). The resulting mixture was allowed to cool to room temperature then concentrated under vacuum to an oil. The crude imide was purified by flash chromatography on silica gel (65×280 mm column) eluted with 2:1 hexane: acetone (note: the crude product was not very soluble in this solvent; the crude product was thus dissolved in acetone (125 mL) and adsorbed onto silica gel (50 g) which was placed at the head of the packed column) collecting 50 mL fractions after a 1.5 L forerun to afford the pure imide (in fractions 9–30) as a colorless liquid. $^1$H NMR: (CDCl$_3$, 600 MHz) δ 4.28–4.38 (1H, m, H$_1$), 3.91 (1H, dd, J=7, 12 Hz, H$_{2'a}$), 3.76 (1H, dd, J=3, 12 Hz, H$_{2'b}$), 2.91 (1H, dd, J=17, 9 Hz, H$_{4α}$), 2.80–2.88 (1H, m, H$_3$), 2.31 (1H, dd, J=17, 4 Hz, H$_{4β}$), 1.34 & 1.33 (6H, 2 d, J=7 Hz, 2CH$_3$s).

Step 2: Chiral Prep HPLC.

Chiral preparative HPLC of the imide was performed on a Chiralpak AD 100×250 mm column packed at 60 bar and eluted with 30% IPA/iso-octane at 300 mL/min, with monitoring at 220 nm, using 1 g injections of sample dissolved in 50:50 hept/IPA. The retention time of the minor diastereomer was approx. 8.4 mins. and the major, positively rotating diastereomer was approximately 10.8 mins.

Step 3: (2S)-2-[(3R)-3-methylpyrrolidin-1-yl]propan-1-ol.

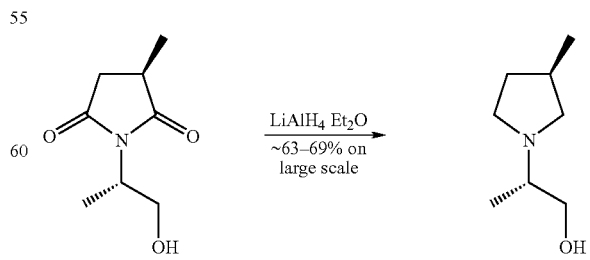

Lithium aluminum hydride (96 mL of 1.0 M solution in ether, 0.096 moles) was added to a cold (ice bath) solution of (3R)-1-[(1S)-2-hydroxy-1-methylethyl]-3-methylpyrrolidine-2,5-dione (8.26 g, 0.048 moles) in anhydrous ether (565 mL). The cold bath was removed and the resulting mixture was stirred at room temperature for 17 hours. The resulting mixture was cooled in an ice bath as water (3.7 mL) was added slowly dropwise (CALIMON: vigorous reaction, gas evolution) followed by 15% NaOH (3.7 mL) and additional water (11.0 mL). The resulting mixture was stirred vigorously for 15 minutes then sonicated for 15 minutes and filtered. The collected solid was washed with ether (2×125 mL; stirred vigorously for 15 minutes then sonicated 15 minutes and filtered) and the combined filtrates were dried (MgSO4), filtered, and evaporated to a light yellow oil (5.76 g). The crude product was purified by flash chromatography on silica gel (65×222 mm column) eluted with 10:7:2:1 ethyl acetate:hexane:methanol:triethylamine collecting 50 mL fractions after a forerun of 750 mL to afford the pure product (in fractions 6–50) as a light yellow liquid. $^1$H NMR: (CDCl$_3$, 600 M) δ 3.54 & 3.32 (2H, 2 dd, J=5, 10 Hz, H$_1$), 3.30 (1H, br s, OH), 2.83 & 2.11 (2H, 2 dd, J=8, 8 Hz, H$_{2'}$), 2.62–2.67 & 2.54–2.59 (2H, 2m, H$_{5'}$), 2.65–2.68 (2H, m, H$_2$), 2.15–2.24 (1H, m, H$_{3'}$), 1.92–1.98 & 1.28–1.34 (2H, 2m, H$_{4'}$), 1.00 (6H, d, J=7 Hz, 2CH$_3$s); $^{13}$C NMR: (CDCl$_3$, 150 MHz) δ 64.54, 58.02, 57.46, 48.87, 32.45, 31.67, 20.24, 12.49; MS (electrospray): m/e 144 (M+H). [α]$_D$−0.5° (c=1.0 in MeOH).

Example 14

Preparation of 2(S)-(3-(S)-methylpyrrolidinyl)-propan-1-ol

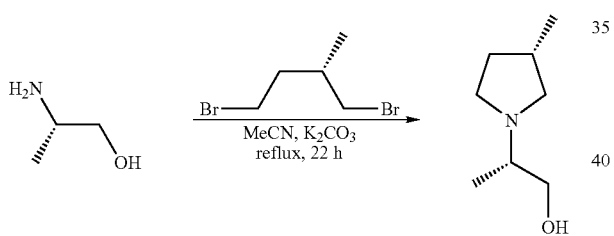

A solution of 2-(S)-methyl-1,4-dibromobutane (2.70 g, 0.012 moles) in anhydrous acetonitrile (8 mL) was added to a mixture of of (S)-(+)-2-amino-1-propanol (0.882 g, 0.012 moles, Aldrich) and potassium carbonate (3.25 g, 0.024 moles) in anhydrous acetonitrile (92 mL). The resulting mixture was refluxed for 22 hours then cooled to room temperature and concentrated under vacuum to an oily white solid. Dichloromethane (50 mL) and saturated aqueous potassium carbonate (10 mL) were added followed by just enough water to dissolve all solid. The layers (upper layer organic, lower layer aqueous) were separated and the aqueous layer was saturated with sodium chloride and extracted with dichloromethane (2×50 mL). The combined organic layers were dried over magnesium sulfate and potassium carbonate, filtered and evaporated to a light yellow liquid. This crude product was purified by column chromatography on silica gel eluted with 10:7:2:1 ethyl acetate:hexane: methanol:triethylamine to afford the title compound as a light yellow liquid. NMR: (CDCl$_3$, 600 MHz) δ 3.52 & 3.32 (2H, 2 dd, J=5, 10 Hz, H$_1$), 3.36 (1H, br s, OH), 2.79 (1H, t, J=8 Hz, H$_{2'a}$), 2.54–2.58 (1H, m, H$_2$), 2.66–2.72 & 2.56–2.62 (4H, 2m, H$_{5'}$), 2.13–2.21 (1H, m, H$_{3'}$), 2.08 (1H, td, J=8 Hz, H$_{2'b}$), 1.92–2.00 & 1.25–1.33 (4H, 2m, & H$_{4'}$), 1.00 (3H, d, J=7 Hz, H$_{3',Me}$), 0.99 (3H, d, J=7 Hz, H$_3$); MS (electrospray): m/e 144 (M+H), 126 (M−OH). [α]$_D$+3.4°.

Example 15

Preparation of (2S)-2-[(3R,4R)-3,4dimethylpyrrolidin-1-yl]propan-1-ol, (2S)-2-[(3S,4S)-3,4dimethylpyrrolidin-1-yl]propan-1-ol, and (2S)-2-[(3S,4R)-3,4dimethylpyrrolidin-1-yl]propan-1-ol

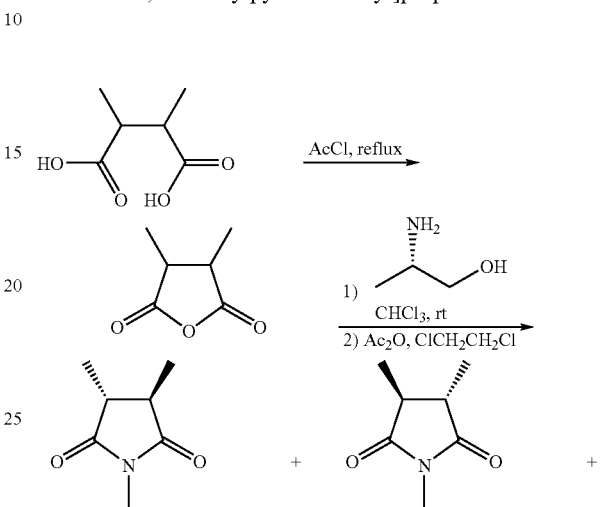

Isomer A
(+)-(S, R, R or S, S, S)

Isomer B
(−)-(S, S, S or S, R, R)

Isomer C
(+)-(S, S, R)

Step 1: A mixture of 2,3-dimethyl succinic acid (21.2 g, 145.1 mmol) and acetyl chloride (80 mL) was heated to reflux for 2.5 h. The resulting solution was cooled to ambient temperature and concentrated. The residue was dissolved in toluene and concentrated thrice. The residue was dissolved in toluene, filtered, and concentrated to give an off-white solid. $^1$H NMR showed a 1:1.5 cis:trans mixture of products, and the crude mixture was used without further purification Step 2: The crude anhydrides (6.0 g, 46.8 mmol), obtained in Step 1, were dissolved in anhydrous dichloromethane (200 mL) and placed under a balloon of nitrogen. Triethylamine (7.2 mL, 51.7 mmol) and (S)-2-aminopropanol (4 mL, 51.4 mole) were added. The reaction initially turned cloudy and then went clear with a clear colorless residue clinging to the sides of the flask. The mixture was stired at ambient temperature for 26.75 hours after which time the reaction was concentrated to an oil. The oil was dissolved in dichloroethane (200 mL), acetic anhydride (22 mL, 233 mmol) added, and the solution was heated to reflux for 18.2 hours. The solution was cooled to ambient temperature and stirred with saturated aqueous sodium bicarbonate. After 1 hour, the mixture was partitioned between dichloromethane and saturated aqueous sodium bicarbonate. The aqueous layer separated and extracted further with dichloromethane. The combined organic layers were washed with brine, dried (MgSO$_4$), filtered, and concentrated. Purification by flash chromatography on silica gel eluted with hexane-ethyl acetate (2:1) afforded a mixture of racemic trans-imides, as a colorless liquid, and a mixture of enriched cis-imide. Chiral separation of the racemic trans imides on a Chiral-Cel® OD™ column (4.6×250 mm), available rom Daicel Industries, Ltd., eluted with 5% EtOH-heptane (20 injections) afforded the imide isomer A (S,R,R or S,S,S); [α]$_D$=+86° (c=1.0, MeOH), and imide isomer B (S,S,S or S,R,R); [α]$_D$=−35.3° (c=1.0, MeOH). The above cis-enriched mixture was further purified by flash chromatography on silica gel eluted with hexane-ethyl acetate (4:1) to afford the imide isomer C (S,S,R); [α]$_D$=+27° (c=1.0, MeOH), and the racemic trans imides.

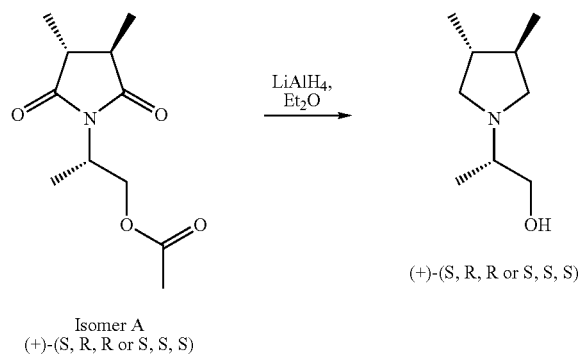

Isomer A
(+)-(S, R, R or S, S, S)

(+)-(S, R, R or S, S, S)

Step 3: Reduction of Isomer A.

To a stirred solution of 1.59 g (7.0 mmol) of imide isomer A, from Step 2 above, in 80 mL of anhydrous diethyl ether was added lithium aluminum hydride (0.8 g, 21.1 mmol). The resulting mixture was placed under a balloon of nitrogen and stirred further for 17.6 hours at ambient temperature. To this mixture was sequentially added, water (0.8 mL), 15% aqueous NaOH solution (0.8 mL), and water (2.4 mL), and then diethyl ether. The resulting mixture was sonicated and the aluminum salts were removed by filtration. The filtrate was dried (MgSO4), filtered, and evaporated to give a clear oil. Purification by flash chromatography on silica gel eluted with ethyl acetate-hexane-methanol-triethylamine (13:5:1:1) afforded the (+)-(S,R,R or S,S,S)-pyrrolidine. $^1$H 500 MHz NMR (CDCl$_3$, δ, ppm) 3.56 (dd, J=10.0, 4.0 Hz, 1H), 3.30 (dd, J=10.0, 7.0 Hz, 1H), 2.87 (dd, J=9.5, 7.5 Hz, 2H), 2.70–2.77 (m, 1H), 2.31 (dd, J=9.0, 7.0 Hz, 2H), 1.64–1.74 (m, 2H), 1.03 (d, J=6.5 Hz, 6H), 1.00 (d, J=6.5 Hz, 3H); MS (electrospray): m/z 158.4 (M+H); [α]$_D$=+44.1° (c=1.0, MeOH).

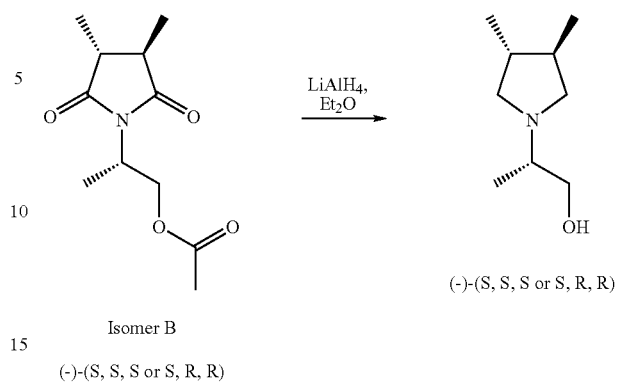

Isomer B (−)-(S, S, S or S, R, R)

(−)-(S, S, S or S, R, R)

Step 4: Reduction of Isomer B.

To a stirred solution of 1.41 g (6.2 mmol) of imide isomer B, from Step 2 above, in 71 mL of anhydrous diethyl ether was added lithium aluminum hydride (0.71 g, 18.7 mmol). The resulting mixture was placed under a balloon of nitrogen and stirred further for 18 hours at ambient temperature. To this mixture was sequentially added, water (0.71 mL), 15% aqueous NaOH solution (0.71 mL), and water (2.1 mL), and then diethyl ether. The resulting mixture was sonicated and the aluminum salts were removed by filtration. The filtrate was dried (MgSO$_4$), filtered, and evaporated to an oily solid. Purification by flash chromatography on silica gel eluted with ethyl acetate-hexane-methanol-triethylamine (13:5:1:1) afforded the (−)-(S,R,R or S,S,S)-pyrrolidine, as a light yellow solid. $^1$H 500 MHz NMR (CDCl$_3$, δ, ppm) 3.54 (dd, J=8.5, 3.5 Hz, 1H), 3.30 (dd, J=8.5, 5.0 Hz, 1H), 2.82 (dd, J=7.5, 6.0 Hz, 2H), 2.62–2.68 (m, 1H), 2.31 (dd, J=7.5, 6.0 Hz, 2H), 1.62–1.70 (m, 2H), 0.99–1.03 (m, 9H,); MS (electrospray): m/z 158.3 (M+H); [α]$_D$=−40.5° (c=1.0, MeOH).

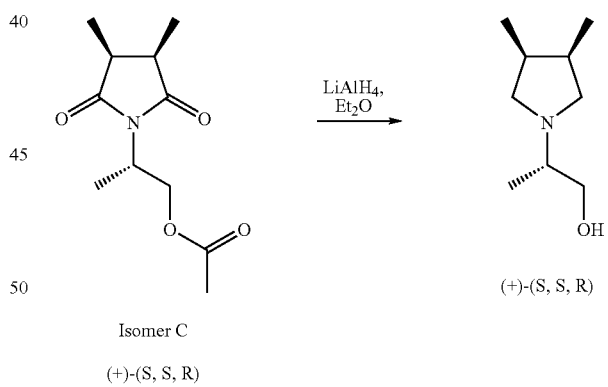

Isomer C
(+)-(S, S, R)

(+)-(S, S, R)

Step 5: Reduction of Isomer C.

To a stirred solution of 0.7 g (3.1 mmol) of imide isomer C, from Step 2 above, in 100 mL of anhydrous diethyl ether was added lithium aluminum hydride (0.35 g, 9.2 mmol). The resulting mixture was placed under a balloon of nitrogen and stirred further for 18.2 hours at ambient temperature. To this mixture was sequentially added, water (0.35 mL), 15% aqueous NaOH solution (0.35 mL), and water (1.1 mL), and then diethyl ether. The resulting mixture was sonicated and the aluminum salts were removed by filtration. The filtrate was dried (MgSO$_4$), filtered, and evaporated to a clear oil. Purification by flash chromatography on silica gel eluted with ethyl acetate-hexane-methanol-triethylamine (13:5:1:1) afforded the (+)-(S,S,R)-pyrrolidine, as a clear oil. $^1$H 500 MHz NMR (CDCl$_3$, δ, ppm) 3.57 (dd, J=10.5, 4.5 Hz, 1H), 3.31 (dd, J=10.5, 7.0 Hz, 1H), 3.00 (dd, J=8.5, 6.5 Hz, 1H), 2.92 (dd, J=8.5, 6.5 Hz, 1H), 2.69–2.73 (m, 1H), 2.18–2.27 (m, 4H), 1.02 (d, J=6.5 Hz, 3H), 0.94 (d, J=6.5 Hz, 3H), 0.93 (d, J=6.5 Hz, 3H); MS (electrospray): m/z 158.3 (M+H); [α]$_D$=+1.9° (c=1.0, MeOH).

Pharmaceutical Composition

As a specific embodiment of this invention, 25 mg of the compound 11a, from Example 11, is formulated with sufficient finely divided lactose to provide a total amount of 580 to 590 mg to fill a size 0, hard-gelatin capsule.

What is claimed is:

1. A compound of the formula:

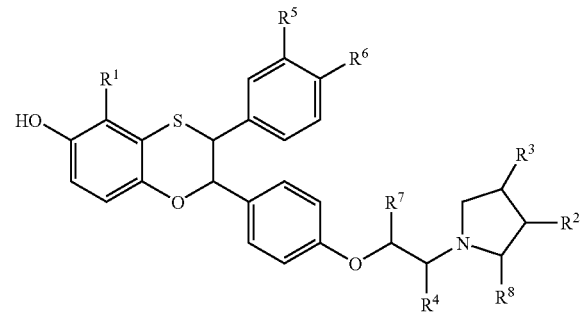

wherein $R^1$ is selected from hydrogen or halo;
$R^2$ is selected from hydrogen, $C_{1-3}$ alkyl, $CH_2F$, $CHF_2$ or $CF_3$;
$R^3$ is selected from hydrogen, $C_{1-3}$ alkyl, $CH_2F$, $CHF_2$ or $CF_3$;
$R^4$ is selected from $C_{1-3}$ alkyl, $CH_2F$, $CHF_2$, $CF_3$, or hydrogen with the proviso that $R^4$ and $R^7$ are not simultaneously hydrogen;
$R^5$ is selected from hydrogen or hydroxyl;
$R^6$ is selected from hydrogen or hydroxyl;
$R^7$ is selected from $C_{1-3}$ alkyl, $CH_2F$ or hydrogen with the proviso that $R^4$ and $R^7$ are not simultaneously hydrogen;
$R^8$ is selected from hydrogen, $C_{1-3}$ alkyl or $CH_2F$;
or a pharmaceutically acceptable salt, stereoisomer, or chiral form thereof.

2. The compound of claim 1 wherein $R^4$ is $CH_3$; or a pharmaceutically acceptable salt, stereoisomer, or chiral form thereof.

3. The compound of claim 2 of the formula:

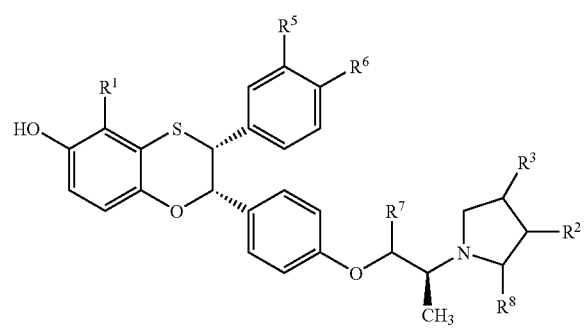

wherein $R^1$ is selected from hydrogen or halo;
$R^2$ is selected from hydrogen, $C_{1-3}$ alkyl, $CH_2F$, $CHF_2$ or $CF_3$;
$R^3$ is selected from hydrogen, $C_{1-3}$ alkyl, $CH_2F$, $CHF_2$ or $CF_3$;
$R^5$ is selected from hydrogen or hydroxyl;
$R^6$ is selected from hydrogen or hydroxyl;
$R^7$ is selected from hydrogen, $C_{1-3}$ alkyl or $CH_2F$;
$R^8$ is selected from hydrogen, $C_{1-3}$ alkyl or $CH_2F$;
or a pharmaceutically acceptable salt, stereoisomer, or chiral form thereof.

4. The compound of claim 3 wherein $R^1$ is selected from the group consisting of hydrogen and fluoro; or a pharmaceutically acceptable salt, stereoisomer, or chiral form thereof.

5. The compound of claim 4 selected from:

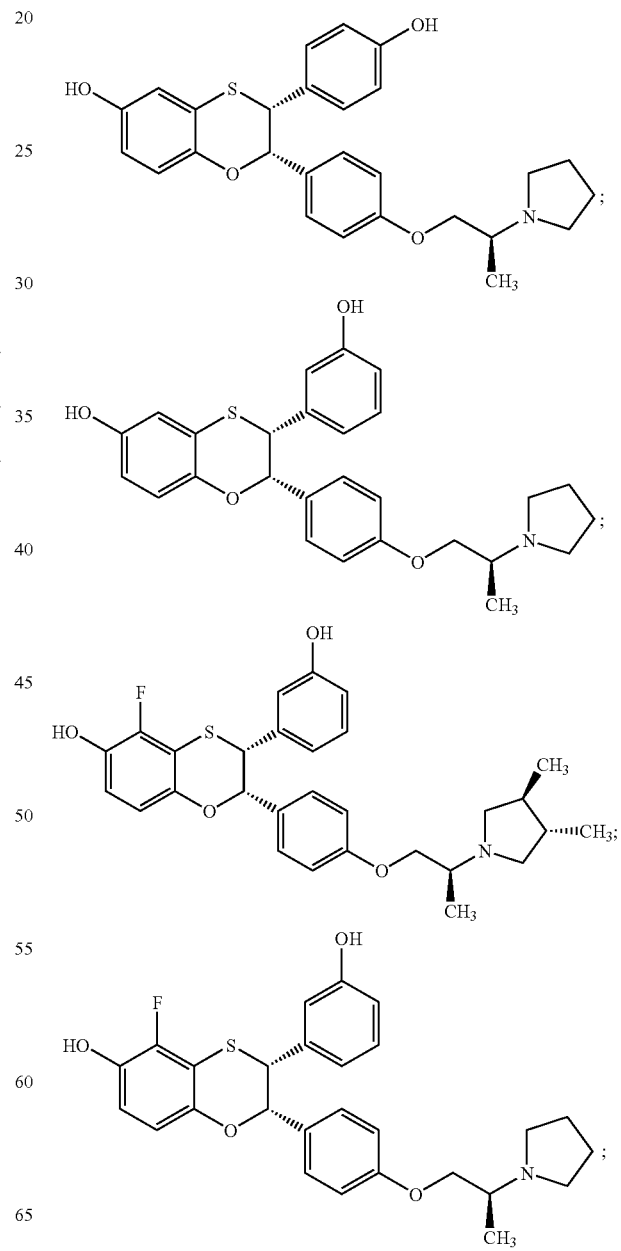

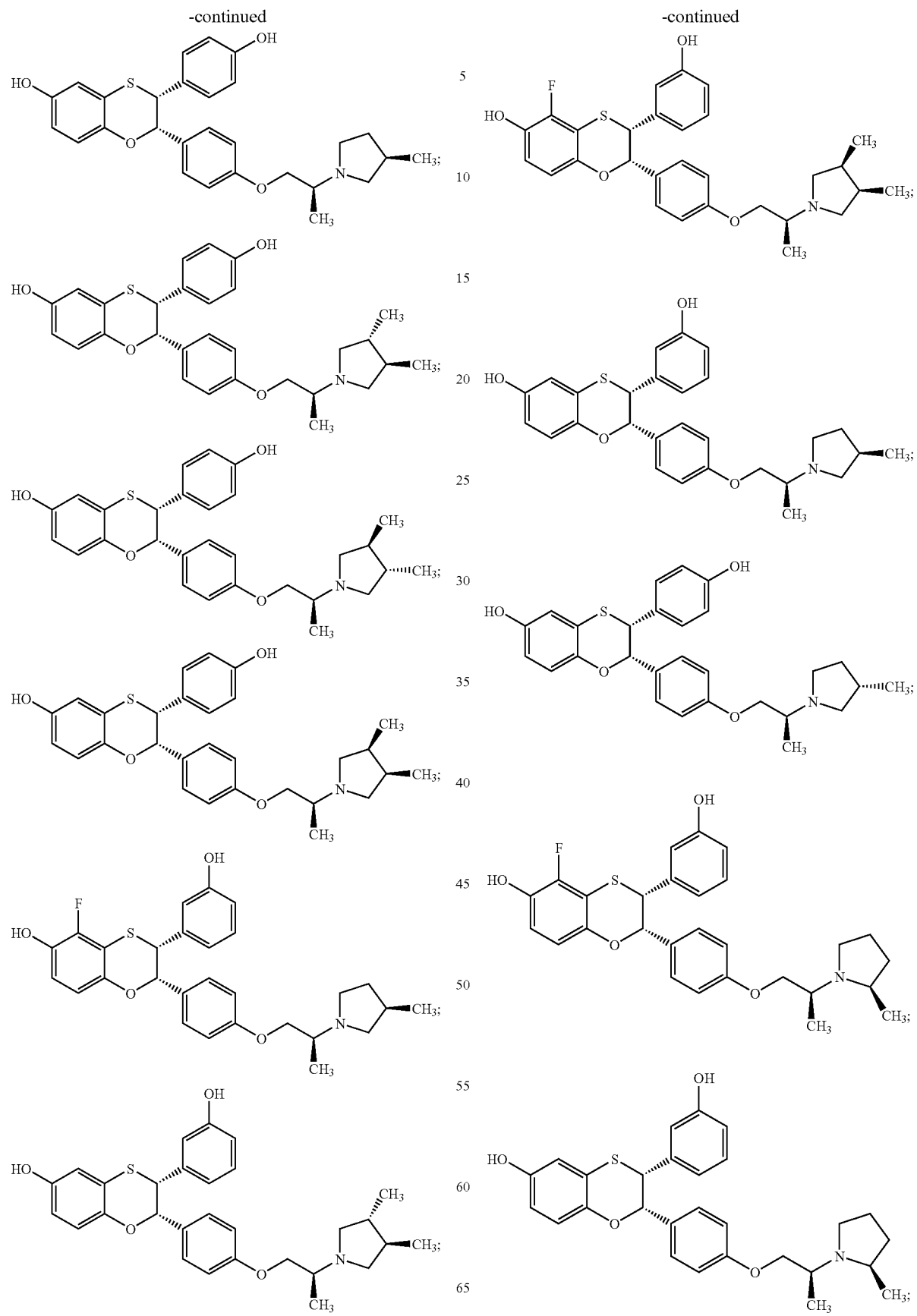

-continued
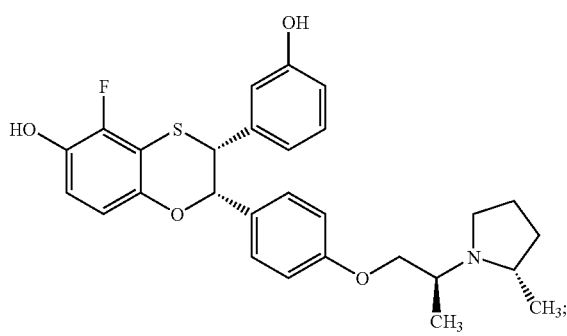
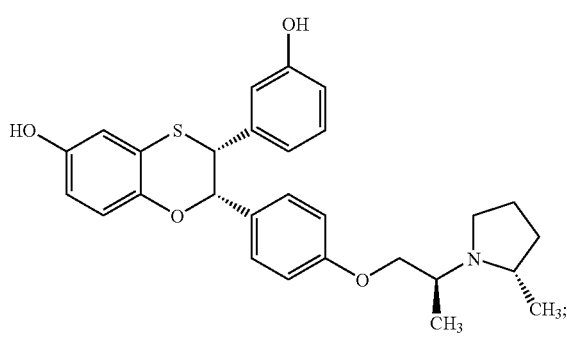
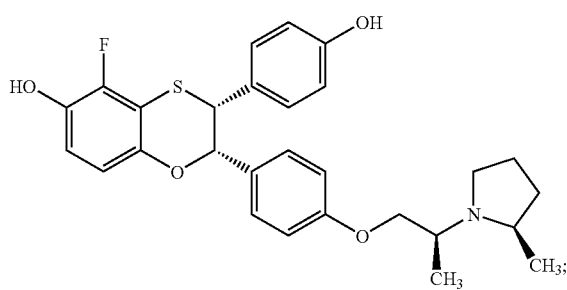
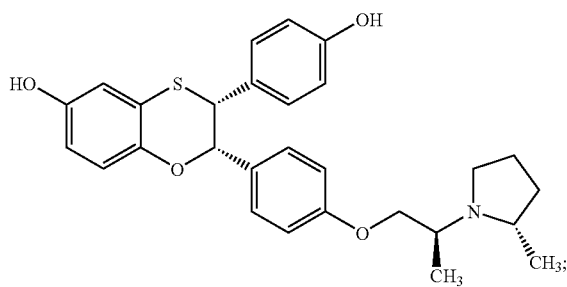
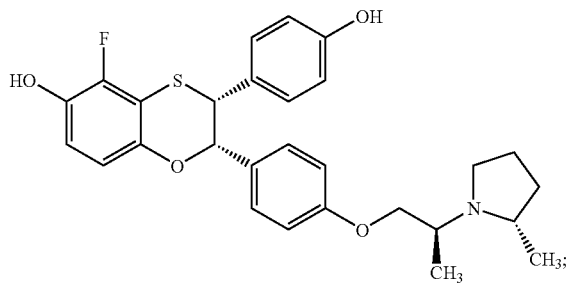
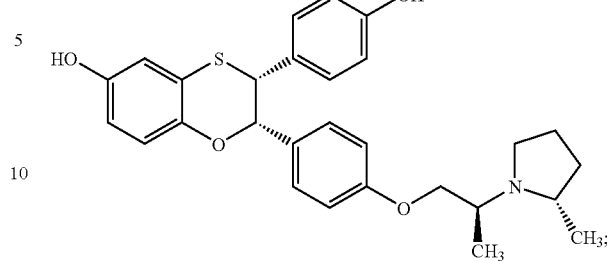
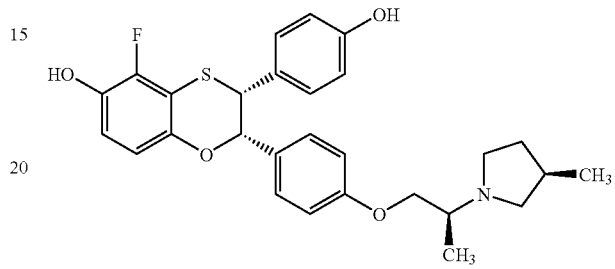
or a pharmaceutically acceptable salt, stereoisomer, or chiral form thereof.
6. The compound of claim 5 which is
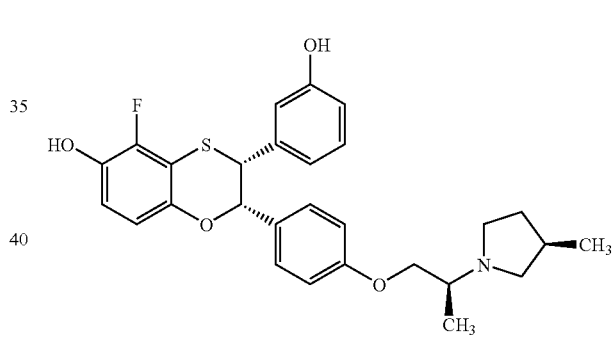
or a pharmaceutically acceptable salt, stereoisomer, or chiral form thereof.
7. The compound of claim 5 which is
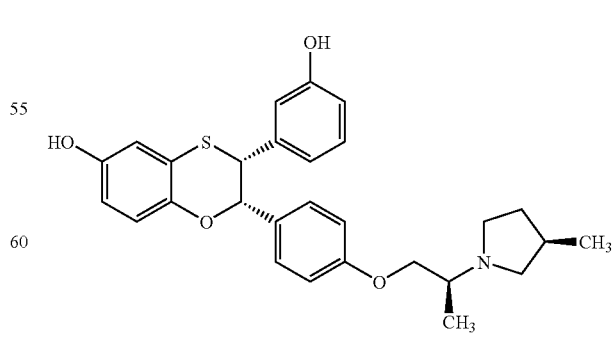
or a pharmaceutically acceptable salt, stereoisomer, or chiral form thereof.

8. The compound of claim 5 which is

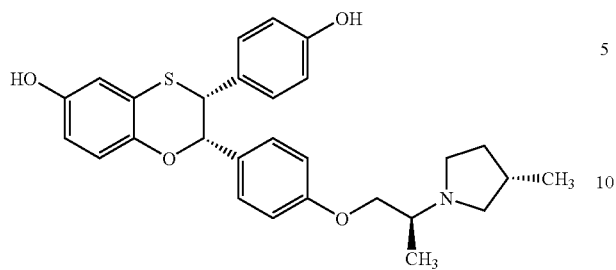

or a pharmaceutically acceptable salt, stereoisomer, or chiral form thereof.

9. The compound of claim 5 which is

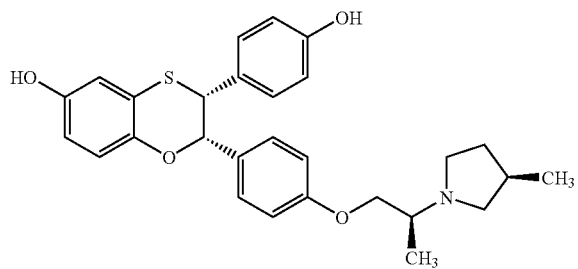

or a pharmaceutically acceptable salt, stereoisomer, or chiral form thereof.

10. The compound of claim 5 which is

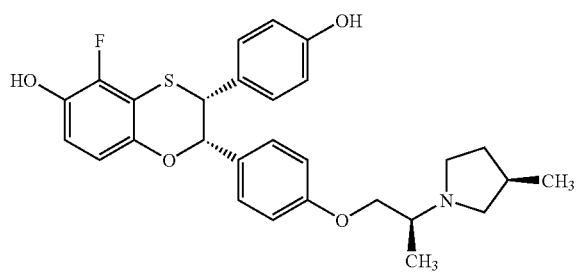

or a pharmaceutically acceptable salt, stereoisomer, or chiral form thereof.

11. The compound of claim 2 of the formula:

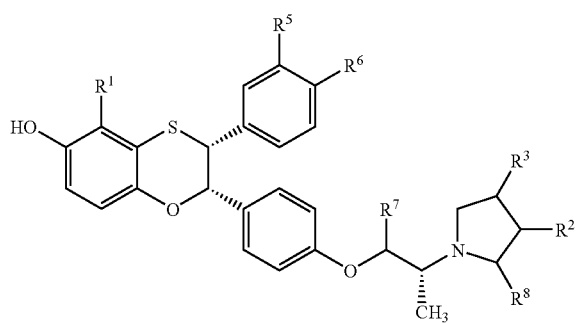

wherein $R^1$ is selected from hydrogen or halo;

$R^2$ is selected from the hydrogen, $C_{1-3}$ alkyl, $CH_2F$, $CHF_2$ or $CF_3$;

$R^3$ is selected from hydrogen, $C_{1-3}$ alky, $CH_2F$, $CHF_2$ or $CF_3$;

$R^5$ is selected from hydrogen or hydroxyl;

$R^6$ is selected from hydrogen or hydroxyl;

$R^7$ is selected from hydrogen, $C_{1-3}$ alkyl or $CH_2F$;

$R^8$ is selected from hydrogen, $C_{1-3}$ alkyl or $CH_2F$;

or a pharmaceutically acceptable salt, stereoisomer, or chiral form thereof.

12. The compound of claim 11 wherein $R^1$ is selected from hydrogen or fluoro; or a pharmaceutically acceptable salt, stereoisomer, or chiral form thereof.

13. The compound of claim 12 selected from:

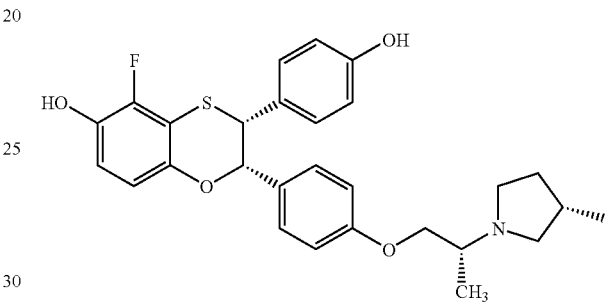

(2S,3R)-5-fluoro-3-(4-hydroxyphenyl)-2-[4-({(2R)-2-[(3S)-3-methylpyrrolidin-1-yl]propyl}oxy)phenyl]-2,3-dihydro-1,4-benzoxathiin-6-ol;

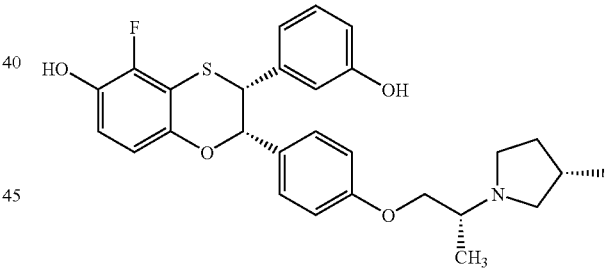

(2S,3R)-5-fluoro-3-(3-hydroxyphenyl)-2-[4-({(2R)-2-[(3S)-3-methylpyrrolidin-1-yl]propyl}oxy)phenyl]-2,3-dihydro-1,4-benzoxathiin-6-ol;

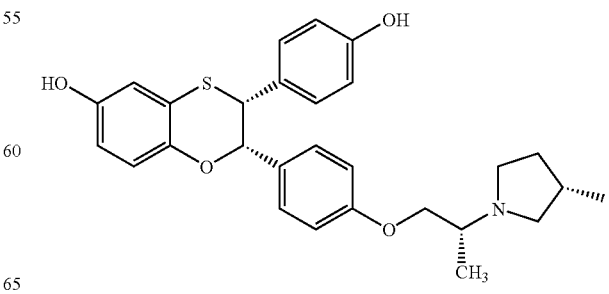

(2S,3R)-3-(4-hydroxyphenyl)-2-[4-({(2R)-2-[(3S)-3-methylpyrrolidin-1-yl]propyl}oxy)phenyl]-2,3-dihydro-1,4-benzoxathiin-6-ol;

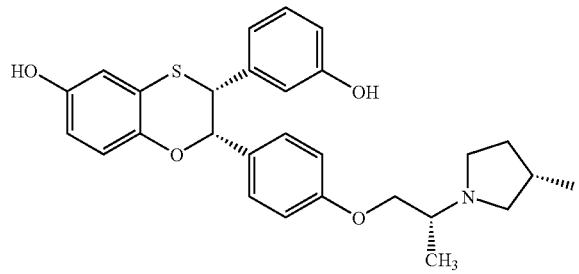

14. A pharmaceutical composition comprising a compound according to claim 1 and a pharmaceuticaly acceptable carrier.

15. A pharmaceutical composition made by combining a compound according to claim 1 and a pharmaceutically acceptable carrier.

16. A process for making a pharmaceutical composition comprising combining a compound according to claim 1 and a pharmaceutically acceptable carrier.

17. A method of eliciting an estrogen receptor modulating effect in a mammal in need thereof, comprising administering to the mammal a therapeutically effective amount of a compound according to claim 1.

18. The method according to claim 17 wherein the estrogen receptor modulation effect is an estrogen receptor agonizing effect.

19. The method according to claim 17 wherein the estrogen receptor agonizing effect is an ERα receptor agonizing effect.

20. The method according to claim 17 wherein the estrogen receptor modulation effect is an estrogen receptor antagonizing effect.

21. The method according to claim 17 wherein the estrogen receptor antagonizing effect is an ERα receptor antagonizing effect.

22. A method of treating a disease in a mammal in need thereof by administering to the mammal a therapeutically effective amount of a compound according to claim 1, wherein said disease is selected from: bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, multiple myeloma, cartilage degeneration, endometriosis, uterine fibroid disease, breast cancer, uterine cancer, prostate cancer, hot flashes, cardiovascular disease, impairment of cognitive function, cerebral degenerative disorders, restenosis, gynecornastia, vascular smooth muscle cell proliferation, obesity or incontinence.

23. The method of claim 22 wherein the disease is osteoporosis.

24. The method of claim 22 wherein the disease is metastatic bone disease.

25. A method of treating an estrogen dependent cancer in a mammal in need thereof by administering to the mammal a therapeutically effective amount of a compound according to claim 1.

26. A pharmaceutical composition comprising a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; an aromatase inhibitor; or a pharmaceutically acceptable salt or mixture thereof.

27. A method of treating osteoporosis comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin-D analogue; a selective serotonin reuptake inhibitor; an aromatase inhibitor; or a pharmaceutically acceptable salt or mixture thereof.

28. A method of treating bone loss comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HG-CoA reductase; an integrin receptor antagonist; an osteoblast anabolic agent; calcitonin; Vitamin D; a synthetic Vitamin D analogue; a selective serotonin reuptake inhibitor; an aromatase inhibitor; or a pharmaceutically acceptable salt or mixture thereof.

29. A method of treating metastatic bone disease comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; an aromatase inhibitor; or a pharmaceutically acceptable salt or mixture thereof.

30. A method of lowering cholesterol comprising administering to a mammal in need thereof a compound of claim 1 and another agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; or a selective serotonin reuptake inhibitor; or a cholesterol ester transfer protein inhibitor; a pharmaceutically acceptable salt or mixture thereof.

31. A method of treating a tamoxifene-resistant breast cancer in a mammal in need thereof by administering to the mammal a therapeutically effective amount of a compound according to claim 1.

32. The method of claim 22 wherein the disease is metastatic breast cancer.

* * * * *